(12) United States Patent
Lu et al.

(10) Patent No.: US 8,442,780 B2
(45) Date of Patent: May 14, 2013

(54) MATERIAL PROPERTY IDENTIFICATION SYSTEM AND METHODS

(75) Inventors: Jia Lu, Iowa City, IA (US); Xuefeng Zhao, Iowa City, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 977 days.

(21) Appl. No.: 12/459,418

(22) Filed: Jul. 1, 2009

(65) Prior Publication Data

US 2010/0049451 A1    Feb. 25, 2010

Related U.S. Application Data

(60) Provisional application No. 61/133,671, filed on Jul. 1, 2008.

(51) Int. Cl.
*G01L 1/00*    (2006.01)

(52) U.S. Cl.
USPC ............................................ 702/42; 600/587

(58) Field of Classification Search ...... 702/42; 600/587
See application file for complete search history.

(56) References Cited

U.S. PATENT DOCUMENTS

| 2003/0220556 A1 | 11/2003 | Porat et al. |
| 2007/0282202 A1 | 12/2007 | Maurice et al. |
| 2008/0058644 A1 | 3/2008 | Sandrin et al. |

FOREIGN PATENT DOCUMENTS

| JP | 11295043 | 10/1999 |

OTHER PUBLICATIONS

Kroon et al. "Estimation of the distributions of anisotropic, elastic properties and wall stresses of saccular cerebral aneurysms by inverse analysis" Proceedings of the Royal Society available online Jan. 2008. pp. 807-824.*
Lu et al. "Inverse elastostatic stress alanysis in pre-deformed biological structures: Demonstration using abdominal aortic aneurysms" Journal of Biomechanics 2007, 693-696. 2006.*
Holzapfel et al. "Biomechanical behavior of the aterial wall and its numerical characterization" Computers in Biology and Medicine, 1998. 377-392.*
J. Lu, X. Zhou, M.L. Raghavan, Inverse Elastostatic Stress Analysis in Pre-Deformed Biological Structures: Demonstration Using Abdominal Aortic Aneurysms. Journal of Biomechanics, 40, 693-696, 2007, Published online: Mar. 17, 2006.
J. Lu, X. Zhou, M.L. Raghavan, Computational Method for Inverse Elastostatics in Anisotropic Hyperelastic Solids, International Journal for Numerical Methods in Engineering, 69, 1239-1261, 2007; Published online: Jul. 31, 2006.
Millan, et al., Morphological characterization of intracranial aneurysms using 3-D moment invariants, IEEE Transactions on Medical Imaging, vol. 26, No. 9, p. 1270-1282, Sep. 2007.
X. Zhou and J. Lu, Inverse Formulation for Geometrically Exact Stress Resultant Shells, International Journal for Numerical Methods in Engineering, vol. 74, p. 1278-1302, 2008; Published online: Oct. 8, 2007.

(Continued)

*Primary Examiner* — Max Hindenburg
*Assistant Examiner* — Renee Danega
(74) *Attorney, Agent, or Firm* — Valauskas Corder LLC

(57) ABSTRACT

The distributive elastic properties in nonlinear structures is characterized using an inverse elastostatic approach of stress analysis using assumed elastic models without knowing the realistic material parameters. Stress distributions are computed independently of strain measurements. A database of pointwise stress and strain data in regions of the nonlinear structure permits the elastic properties of the structure to be characterized point-by-point to provide the property distribution.

7 Claims, 30 Drawing Sheets
(27 of 30 Drawing Sheet(s) Filed in Color)

OTHER PUBLICATIONS

J. Lu, X. Zhou, M.L. Raghavan, Inverse Method of Stress Analysis for Cerebral Aneurysms, Biomech Model Mechanobiol, vol. 7, p. 477-486, 2008; Published online: Nov. 8, 2007.

Raghavan, et al., Regional Distribution of Wall Thickness and Failure Properties of Human Abdominal Aortic Aneurysm, Journal of Biomechanics, vol. 39, p. 3010-3016, 2006; Published online: Dec. 12, 2005.

Manduca, et al., Magnetic Resonance Elastography: Non-invasive Mapping of Tissue Elasticity, Medical Image Analysis vol. 5, p. 237-254, 2001.

Metwalli, Industrial Applications of Computer Image Processing, Computers & Industrial Engineering, New York, vol. 11, iss. 104, p. 608-612, 1986.

Roham et al., Design and Fabrication of a New Tactile Probe for Measuring the Modulus of Elasticity of Soft Tissues, Sensor Review, vol. 27, No. 4, p. 317-323, 2007.

Heng, et al., Peak wall stress measurement in elective and acute abdominal aortic aneurysms, Journal of Vascular Surgery, vol. 47, iss. 1, p. 17-22, Jan. 2008; Published online: Nov. 30, 2007.

* cited by examiner

MATERIAL PROPERTY IDENTIFICATION SYSTEM AND METHODS

PRIORITY STATEMENT

This application claims priority from U.S. Provisional Application Ser. No. 61/133,671 filed Jul. 1, 2008.

STATEMENT CONCERNING FEDERALLY SPONSORED RESEARCH

This invention was made with government support under CMS 03-48194 awarded by the National Science Foundation. The government has certain rights in the invention.

FIELD OF THE INVENTION

The present invention relates generally to the identification of material elastic properties, and more particularly to a system and methods for identifying the distribution of heterogeneous anisotropic elastic properties in soft tissue or thin-walled tissue structures such as cerebral aneurysms.

BACKGROUND OF THE INVENTION

Elastic properties of materials used in many fields are often critical to the design, operation, or safety of the materials. In the field of manufacturing, the elastic properties of manufactured materials and their components often must meet defined specifications which are essential to the utility and safety of the manufactured products. In the medical field, elastic properties of biological tissues are important for tissue function. In the field of construction, the elastic properties of construction materials including foundation soils are important to the design criteria and safety considerations for engineered structures, roads, dams, excavations, and earthworks. In all these fields, it is useful and often essential to have an efficient, reliable means to obtain elastic properties of the materials in question. For medical applications, it is often desirable that the method be non-destructive and be based on in vivo diagnostic data.

Current techniques used to measure the properties of material sheets suffer from two deficiencies. First, currently measurement techniques are usually invasive and destructive and therefore not ideal for in vivo measurements. Second, existing techniques only measure overall (average) properties over the material specimen, thus failing to account for the heterogeneous distribution of properties.

In general, the stress in a deformable solid depends on the applied load, displacement constraints, geometry, and material property. There is, nevertheless, a class of problems in which the stress depends only on the load, boundary condition and geometry, but not the material property. Systems as such are called statically determined. Static determinacy plays a crucial role in experimental characterization of elastic properties, because in a statically determined system the stress can be obtained without knowing the material properties in question. The stress data acquired from equilibrium, together with the strain date computed from measured deformation, finishes the data base for quantifying the material property. The classical material characterization method, the specimen test, makes use of uniform stress which is a fundamental type of statically determined stress field. This invention hinges on another family of static determinate system, the membrane structure load by transverse pressure. Static determinacy in membrane structures has long been long recognized. For example, it is known that the wall tension in a pressurized spherical membrane follows the Laplace formula $T=pR/2$ (T: wall tension, p: transmural pressure, R: inner radius) in which the material property plays no role. Static determinacy in membranes stems from the characteristics of membrane equilibrium. A membrane is a thin material body of which the thickness is much smaller than the other dimensions. Due to thinness, a membrane has negligible resistance to bending and transverse shear. Thus, the stress is locally in a plane stress state, having three nonzero components. When the membrane surface is curved, the equilibrium equation gives rise to three component equations. Thus, the equilibrium equations are closed. If the membrane is subjected to traction boundary alone (Neumann problem), the wall stress is completely independent of the material properties. When displacement boundary conditions are present (Dirichlet or mixed problems), the equilibrium equations are no longer closed and stress solution requires the knowledge of material's stress-strain relation (constitutive equation). However, if the membrane is sufficiently deep (say the height is comparable to the diameter), the influence of material exists only in a thin boundary layer; the far field stress is asymptotic to the material-independent static distribution. Thus, for practical purposes, curved membranes can be viewed as statically determinate even at the presence of boundary constants.

What is needed is a non-invasive and non-destructive system and methods that can identify material properties such as those in anisotropic heterogeneous nonlinear, elastic materials. The present invention satisfies this demand.

SUMMARY OF THE INVENTION

The present invention is a system and methods of identifying material properties in thin-walled structures. Example of application includes identifying the properties of cerebral aneurysm wall. Knowledge of aneurysm wall property is fundamental to understanding rupture risk.

Cerebral aneurysms are focal dilatations of the intracranial arterial wall that usually develop in or near the circle of Willis or cerebral arterial circle. Non-complicated cerebral aneurysms are typically thin-walled. Their diameters range from a few to a few tens of millimeters while the wall thicknesses range from tens to hundreds of micrometers. In their service environment, these lesions are best described as elastic membranes subjected to transmural pressure and hemodynamic shear stress. While the long term growth and remodeling are likely modulated by the lumen shear stress, the sudden bleed or rupture is believed to be caused by the pressure induced wall stress. Rupture likely occurs at the spot where the wall stress exceeds the wall strength. Historically, the size has been used as an indicator for evaluating rupture risk; recently it is believed that shape may provide a more reliable prediction.

Fundamental to stress and strain prediction is the constitutive behavior of wall tissue. However, delineating the constitutive equation of aneurysm tissue, in particular, experimental determination of the material parameters, presents some significant challenges. The lesion wall typically consists of multiple layers of type I and III collagen fibers with varying orientations that form two-dimensional networks. Variation in microstructure and remodeling history gives rise to spatially varying stiffness and symmetry characteristics. At the continuum level, aneurysm tissue is typically characterized as nonlinear, anisotropic, and heterogeneous over finite strain. Among these characteristics, heterogeneity perhaps poses the most difficulty to experiments. Traditional approaches such as specimen tests and optimization-based identification methods have their respective limitations when dealing with heterogeneous materials.

The present invention proposes a pointwise identification method that permits a pointwise characterization of the heterogeneous properties in nonlinear membranes. The key difference compared to the usual optimization methods lies in membrane stress analysis—the membrane inverse elastostatic method—which enables stress prediction without invoking the material property in question. Consistent with the usual experimental practice, material parameters are characterized directly from pointwise stress-strain data, in contrast to an indirect estimation from, for example, displacement response. The present invention can sharply identify heterogeneous properties. More importantly, the present invention opens a pathway for developing noninvasive techniques for characterizing thin tissues in their service environment. This may enable the identification of wall properties at multiple time points during their life, and thus delineate the property evolution due to growth and remodeling. Information as such may shed light on understanding the natural history of the lesions.

Numerical simulation is used to verify the feasibility of identifying the heterogeneous properties in cerebral aneurysms using in vitro inflation test. A finite element method is used to generate deformed configurations; the deformed geometries and the corresponding pressures are taken as "experimental data", from which the prescribed material parameters are identified. The test is conducted on a realistic sac constructed from CT images. The wall material is assumed to follow an anisotropic hyperelastic function—the Holzapfel model. To introduce heterogeneity, the stiffness parameters are assigned to vary spatially in a prescribed pattern. The Holzapfel model, although not entirely based on physical data, incorporates the essential mechanical features and some best known information about cerebral aneurysms.

The present invention includes inverse elastostatic finite element formulations (FEIEM) for membrane and shell structures to determine wall stress of a membrane structure point-by-point, otherwise referred to herein as "pointwise". The inverse approach formulates the weak form directly on the known deformed configuration. The stress in the given deformed state is determined by means of finding an inverse motion under an assumed elasticity model. The stress-free configuration so obtained corresponds to a kinematically compatible configuration which can be brought back to the known deformed configuration upon the application of the load. The assumed material model affects the predicted stress-free configuration, but has a minimal influence on the stress values due to static determinacy. Simulations demonstrate such an insensitivity to material models in both membranes and shells. The advantage of the inverse method, in the context of material characterization, is that it enables the stress to be found without invoking the material property in question, and thus, collect the stress distribution without coupling with parameter regression.

FEIEM takes as the input data a deformed configuration of the membrane structure and the corresponding pressure load, and computes the wall stress without knowledge of the stress-free (i.e., the deflated) configuration. FEIEM capitalizes on the static determinacy of membrane equilibrium. It assists in determining the stress distribution using an assumed material model without a priori knowledge of the material parameters in question. By FEIEM, the wall stress can be acquired independently of strain measurements and the material properties in question.

The pointwise identification method (PWIM) hinges critically on the inverse elastostatic stress analysis. Conceptually, PWIM works as follows. Suppose that a series of deformed configurations of a membrane sac and the corresponding pressures are measured. Then, in each configuration the stress distribution is computed using the inverse elastostatic method, which takes the deformed geometry and the pressure as input. As discussed previously, the method introduces an assumed material model, but the computed stress is expected to be independent of or insensitive to the applied model. In implementation, the sensitivity is checked numerically and parameter regression is performed only in regions where the stress is indeed insensitive. The membrane strain is determined from the measured surface deformation. In this manner, at any point a set of stress-strain data is acquired which embodies the local elastic property. These stress-strain data are subsequently fit pointwise to a proper constitutive model to delineate the local property. This paradigm has been validated using a hyperelastic balloon, where the surface deformation was registered by tracking a surface mesh.

The present invention utilizes a motion acquisition system for strain measurement. In one embodiment, a camera-based photogrammetry 3-D reconstruction system was employed. It is contemplated that image registration methods that can provide material point-to-point correspondence through a series of images can also be employed for strain measurement.

The pointwise material properties are obtained, by way of nonlinear regression, from independently acquires stress and strain data. The present invention therefore can sharply delineate the distribution of material properties. By design, the regression step is independent of the stress and strain computations. Therefore, the present invention decouples the stress solution and the parameter regression to render a simpler computation structure.

The independently acquired stress and strain data may be compiled into a database that allows for the examination of stress-strain properties prior to parameter regression. Examining the stress-strain properties prior to parameter regression is valuable in the determination of proper constitutive models for the material. For example, the co-axial condition between stress and strain can be examined to evaluate whether or not the material is isotropic (namely, the properties are direction-independent).

Since the acquisition of stress and strain data is based solely on the deformed geometries in different deformed configurations of a membrane structure, the present invention allows for non-invasive and non-destructive identification when combined with optic-based or dynamic image-based ("4-D") geometry reconstruction techniques. In addition, the present invention is capable of identifying elastic properties without the knowledge of the stress-free configuration, which is often difficult to obtain in medical applications. Therefore, the present invention may identify the in vivo elastic properties in thin-walled biological structures, such as human aneurysms, for dynamic CT or MRI images and blood pressure data.

In one embodiment, the present invention delineates the distributive elastic properties in a thin-walled membrane structure including a plurality of configurations by computing stress in each configuration individually using finite element inverse elastostatic method independently of the wall elastic property of the membrane structure. Computing stress includes the application of a fixed displacement boundary in each configuration individually. A fixed boundary will induce a thin boundary layer in which the stress depends on the material model used for computation, and this boundary layer should be avoided in parameter-identification. A sensitivity analysis is performed to identify regions where the stress is insensitive to material models. Strain variables in each configuration are calculated from a reconstructed deforming surface mesh. Calculating kinematic variables includes providing a slightly pressurized configuration as the reference, ascertaining the in-plane stretch from the reference geometry, and establishing strain invariants. Stress-strain properties are then examined to select an appropriate energy function. Obtaining the stress-strain properties includes postulating a strain energy that depends on the surface deformation gradient and characterizing the form of the function form via experiments. Obtaining the stress-strain properties may also include deducing the surface energy by reduction where the three-dimensional strain energy function of the material is known. Finally, the best fit material parameters are obtained pointwise by nonlinear regression, wherein the elastic parameters at every Gauss point may be supplied.

It is contemplated that any or all of the method steps to identify material properties of elasticity pointwise can be performed by a general computer system and a motion acquisition system. A general computer system according to the present invention includes a central processing unit (CPU), a read-only memory (ROM), a random access memory (RAM), and a memory hard disk, all interconnected by a system bus, and a software for finite element inverse elastostatic computation. The memory hard disk serves as a storage device and may further include the database of compiled stress and strain data. The motion acquisition system may be camera-based, in which the deformed mesh are reconstructed by photogrammetry techniques; or imaged-based in which the deformed mesh are predicted using image analysis techniques.

An object of the present invention is to provide a system and methods that has the capability of delineating distributive properties pointwise.

Another object of the present invention is to provide a system and methods applicable to material testing, for example, in research and development or quality assurance.

Yet another object of the present invention is to provide diagnostic information for biological soft tissue organs, such as aneurysm, bladder, diaphragm, pericardium and cornea.

Another object of the present invention is to provide a non-invasive and non-destructive image analysis that is cost effective and permits in vivo analysis and diagnostics.

Yet another object of the present invention is to provide a system and methods that analyzes heterogeneous materials.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF EMBODIMENTS OF THE INVENTION

Figure 1:
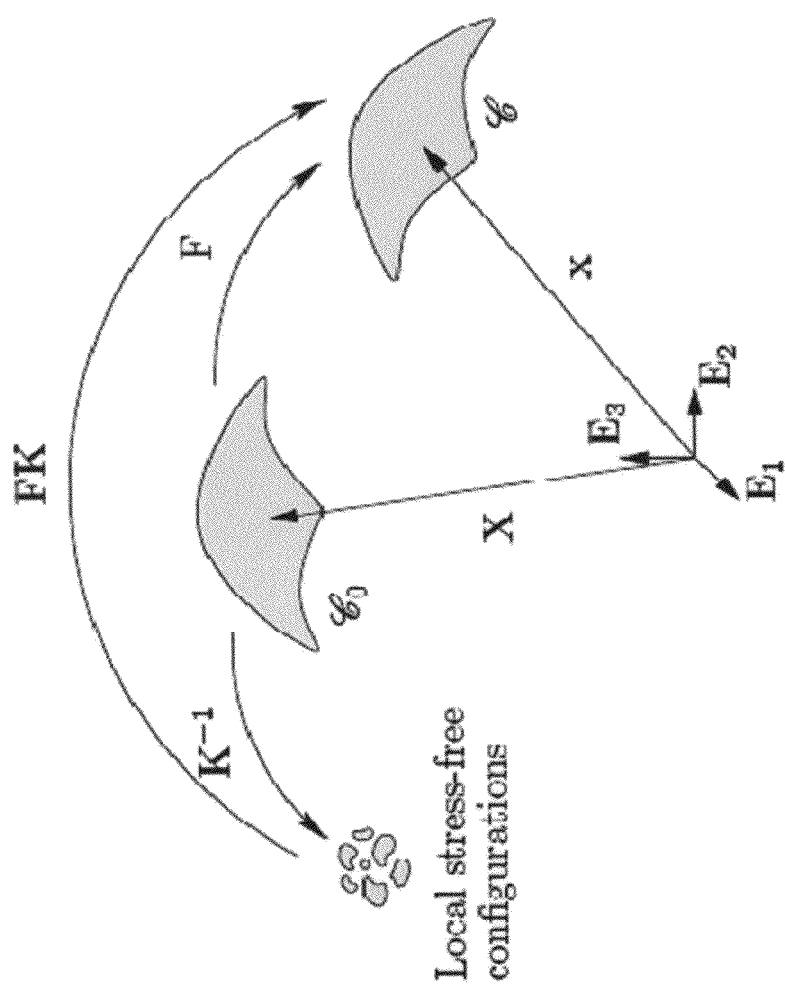
FIG. 1 is a graphical illustration of the kinematic map according to the present invention.

For purposes of this application, the present invention is discussed in reference to identifying elastic properties in a membrane structure, but the present invention is applicable to identifying other material properties, such as visco-elastic and plasticity. A method is devised according to the invention and is referred to herein as the pointwise identification method (PWIM) for identifying the local elastic properties of thin membranes. The theoretical and computational developments of the pointwise identification method are discussed. Following the theoretical and computational developments, the method is validated by performing a physical test on a rubber balloon. The balloon is inflated to a series of pressurized configurations, and a surface mesh that corresponds through all the deformed states is derived using a camera-based photogrammetry technique. In each configuration, the wall tension is computed by the finite element inverse elastostatic method, and the in-plane stretch relative to a slightly pressurized configuration is computed with the aid of finite element interpolation. Based on the examination of the stress-strain characteristics, the Ogden model is employed to describe the material behavior of the balloon. The elastic parameters at every Gauss point in a selected region are identified simultaneously. To verify the predictive capability of the identified material model, the deformation under a prescribed pressure is predicted using the finite element method and is compared to the physical measurement. The experimental results indicated that the method according to the present invention can effectively delineate the distributive elastic properties in the balloon wall.

A membrane is a thin material body of which the thickness is much smaller than the other dimensions. Due to thinness, a membrane has negligible resistance to bending and transverse shear. Thus, it is modeled as a deformable surface that sustains loads by virtue of surface tension. There are numerous ways to present the membrane equations, but for purposes of this application, tensorially covariant forms based on convected coordinates are the most convenient. In this embodiment, the surface is parameterized by surface coordinates $\xi^\alpha$ ($\alpha=1, 2$) in which a pair of coordinates $P=(\xi^1, \xi^2)$ is regarded as the same material point during the deformation. The position vector of the material point P in a deformed configuration $\mathscr{C} \in R^3$ has a position vector denoted by $x=x(P)$. The tangent vectors of the coordinate curves:

$$g_\alpha = \frac{\partial x}{\partial \xi^\alpha} \tag{1}$$

form the basis of the surface tangent space at x (P). An infinitesimal line element is given by $dx = g_\alpha d\xi^\alpha$, and its length is determined from the first fundamental form:

$$ds^2 = dx \cdot dx = g_{\alpha\beta} d\xi^\alpha d\xi^\beta, \quad g_{\alpha\beta} = g_\alpha \cdot g_\beta. \tag{2}$$

The summation convention applies to repeated indices. The coefficients $g_{\alpha\beta}$ constitute the components of the surface metric tensor. The contravariant surface basis vectors $\{g^\alpha, \alpha=1,2\}$ are defined by the relation $g^\alpha g_\beta = \delta^\alpha_\beta$, $g^\alpha \cdot n = 0$ where n is the outward unit normal vector of the surface. The dot product $g^\alpha g_\beta$ gives the components $g_{\alpha\beta}$ of a tensor which is inverse to the metric tensor, i.e., $g_{\alpha\beta} g^{\beta\gamma} = \delta^\alpha_\gamma$. The kinematic variables depend on the configuration in which they are characterized. The position vector, surface basis, contravariant basis, the components of the metric tensor, and the inverse metric tensor on the stress-free reference configuration $\mathscr{C}_0 \in R^3$, provided such a configuration can be identified, are denoted by $X(P)$, $G_\alpha$, $G^\alpha G_{\alpha\beta}$, and $G^{\alpha\beta}$, respectively.

The surface deformation gradient, which maps the surface tangent vectors at $X(P)$ in $\mathscr{C}_0$ to the tangent vectors at $x(P)$ in $\mathscr{C}$ is:

$$F = g_\alpha \otimes G^\alpha \tag{3}$$

The tensor F, regarded as a linear operator in 3-D space, is singular. However, it can be understood as a nonsingular linear operator on vectors lying in the tangent plane at X(P). In this sense, the inverse deformation gradient $F^{-1}$ is:

$$F^{-1} = G_\alpha \otimes g^\alpha \tag{4}$$

The Cauchy-Green deformation tensor associated with F is the surface tensor at X(P) given by:

$$C = F^T F = g_{\alpha\beta} G^\alpha \tag{5}$$

The constitutive equation of a hyperelastic membrane is described by a strain energy function where an energy density is a per unit undeformed reference area. The specific form of the energy function can be established in several ways. If the 3-D strain energy function of the material is known, the surface energy can be deduced by reduction. Alternatively, one can directly postulate a strain energy that depends on the surface deformation gradient, and characterize the function form by experiments or some other means. For purposes of this application, the second approach is followed. Starting from the assumption $w=w(F)$, the invariant requirement under superposed rigid body motion further requires that F enter the energy function through C. If the membrane is isotropic, the material isotropy renders:

$$w = w(I_1, I_2) \tag{6}$$

where $I_1 = \mathrm{tr} C$ and $I_2 = \det C$ are the two principal invariants of tensor C. The invariants in tensorially invariant forms are expressed as:

$$I_1 = g_{\alpha\beta} G^{\alpha\beta}, \tag{7}$$

$$I_2 = \frac{g}{G}$$

where g and G are the determinants of the matrices $[g_{\alpha\beta}]$ and $[G_{\alpha\beta}]$, respectively. The fundamental kinetic variable in the membrane theory is the tension:

$$t = \int_{-\frac{h}{2}}^{\frac{h}{2}} \sigma dh = t^{\alpha\beta} g_\alpha \otimes g_\beta, \tag{8}$$

$$t^{\alpha\beta} = t^{\beta\alpha} \approx h \sigma^{\alpha\beta},$$

where $\sigma^{\alpha\beta}$ are the components of Cauchy stress tensor, and h is the current thickness of the membrane. In the sequel, the tension tensor will also be referred to as the wall stress, or simply stress. Properly invariant stress function can be derived with the aid of the referential resultant:

$$T = F^{-1}(Jt)F^{-T}, \quad J = \sqrt{\frac{g}{G}} \tag{9}$$

which corresponds to the 2nd Piola-Kirchhoff stress S in the 3-D theory. Since $F^{-1}g_\alpha = G_\alpha$, as evidenced by Equation (4), it is clear that $T = Jt^{\alpha\beta}G_\alpha \otimes G_\beta$. Namely, the components $T^{\alpha\beta}$ differ from $t^{\alpha\beta}$ only by the area factor J. The standard argument involving the balance of mechanical power concludes that:

$$T = 2\frac{\partial w}{\partial C} = 2\frac{\partial w}{\partial g_{\alpha\beta}} G_\alpha \otimes G_\beta. \tag{10}$$

It follows that, in components, $$T^{\alpha\beta} = Jt^{\alpha\beta} = 2\frac{\partial w}{\partial g_{\alpha\beta}}.$$

For an isotropic membrane:

$$Jt^{\alpha\beta} = 2\frac{\partial w}{\partial I_1} G^{\alpha\beta} + 2I_2\frac{\partial w}{\partial I_2} g^{\alpha\beta}. \tag{11}$$

In the convected system, the principal invariants of the stress tensor can be computed by:

$$J_1 = tr(t) = t^{\alpha\beta}g_{\alpha\beta}, \quad J_2 = det(t) = det[t^{\alpha\beta}]det[g_{\delta\gamma}]. \tag{12}$$

Note that these expressions are invariant under the change of surface coordinates.

Thin membranes typically collapse when unloaded. They can have multiple stress-free configurations which may not attain a smooth convex shape. To develop a theoretical framework suitable for parameter identification, it is imperative to have a constitutive description that permits a stressed configuration to be used as the reference. This can be achieved using the notion of local stress-free configuration, which associates each infinitesimal material element with a stress-free configuration that can be reached independently of the surrounding material. The stress-free state of the material body is a virtual configuration comprised of the union of the local configurations. The energy function at each material point is characterized with respect to the local stress-free state, whereas the deformation is measured relative to the chosen reference configuration. In this manner, the local stress-free configuration will enter the constitutive law as model parameters. In what follows, it is shown that it can be effectively represented by a Riemannian metric tensor endowed to the reference configuration.

With reference to FIG. 1, let $K^{-1}$ be the local deformation that elastically releases the stress in an infinitesimal surface element at point P and brings the material element to a local stress-free configuration. The map $K^{-1}$ is defined relative to a reference configuration which is not necessarily stress-free. With a slight abuse of notation, this reference configuration is still denoted by $\mathscr{C}_0$, and the associated kinematic variables are denoted by capital letters. The local map $K^{-1}$, regarded as a linear transformation on the tangent vectors at $X(P) \in \mathscr{C}_0$, can be determined if its action on two linearly independent tangent vectors are known. If ($\mathbf{G}_1 d\xi^1$, $\mathbf{G}_2 d\xi^2$) are the images of the line elements ($G_1 d\xi^1, G_2 d\xi^2$), respectively, $K^{-1}$ can be written as:

$$K^{-1} = \mathbf{G}_\alpha \otimes G^\alpha. \tag{13}$$

It should be noted that the tensor $K^{-1}$ is not the gradient of a global mapping. Moreover, since the local configuration is stress-free, any arbitrary re-orientation remains stress-free and thus, the local configuration $K^{-1}$ is determined to within a left rotation.

Under the local relaxation the line element $dX = G_\alpha d\xi^\alpha$ is mapped into $K^{-1}dX = \mathbf{G}_1 d\xi^1 + \mathbf{G}_2 d\xi^2$. The relaxed length is given by:

$$dS_0^2 = (K^{-1}dX) \cdot (K^{-1}dX) = dX \cdot (K^{-T}K^{-1})dX. \tag{14}$$

The tensor is interpreted as:

$$\mathbf{G} := K^{-T}K^{-1} = \mathbf{G}_{\alpha\beta} G^\alpha \otimes G^\beta, \quad \mathbf{G}_{\alpha\beta} = \mathbf{G}_\alpha \cdot \mathbf{G}_\beta \tag{15}$$

as a Riemannian metric tensor on $\mathscr{C}_0$ that describes the unstressed geometry of material elements. The metric tensor is a local property of the reference configuration; it varies from point to point. The rotation indeterminacy of the local configuration, which presents in $K^{-1}$, is eliminated in the metric representation.

During a normal deformation $\mathscr{C}_0$ the tensor to be used in the constitutive equation is FK where F is the regular deformation gradient relative to the reference configuration $\mathscr{C}_0$. Starting from $\omega = \omega(FK)$, the invariant requirement renders:

$$\omega = \omega(K^T F^T FK). \tag{16}$$

The rotational indeterminacy implies $\omega = \omega(QK^T F^T FKQ^T)$ for any rotation tensor Q. This condition dictates that the energy function depend on the principal invariants $I_1$ and $I_2$ of the tensor ($K^T F^T FK$). A straight-forward computation shows:

$$I_1 = tr(K^T F^T FK) = g_{\alpha\beta} \mathbf{G}^{\alpha\beta}$$

$$I_2 = det(K^T F^T FK) = g/\mathbf{G}, \quad \mathbf{G} = det(\mathbf{G}_{\alpha\beta}) \tag{17}$$

It is now clear that the local configuration enters the constitutive equation through the components of the metric tensor $\mathbf{G}$. This representation is useful for parameter identification. In the case where a global stress-free configuration cannot be attained experimentally, the components $\mathbf{G}_{\alpha\beta}$ become unknown model parameters which may be identified from experiments. The metric tensor so obtained may not satisfy the geometric compatibility condition even if a globally compatible stress-free configuration exists. It is noted that, although rotational indeterminacy of $K^{-1}$ renders an isotropic function form, the constitutive approach described herein does not preclude anisotropic material. Anisotropic properties can be introduced by the inclusion of appropriate structural tensors in the constitutive equation, wherein the ensuing function can be rendered covariant, namely invariant with respect to the reference frame.

The inverse elastostatic method is a family of methods for solving finite strain elasticity problems in which a deformed configuration and the corresponding loads are given, while the undeformed configuration and the stress in the deformed state are sought. The inverse method employed in the embodiment described herein addresses the following problem: given a deformed configuration of a pressurized membrane and the corresponding pressure, find the stress in the deformed configuration that satisfies the equilibrium equation:

$$\frac{1}{\sqrt{g}}(\sqrt{g}\, t^{\alpha\beta} g_\alpha)_{,\beta} + pn = 0, \qquad (18)$$

and appropriate boundary conditions. In Equation (18), g=det ($g_{\alpha\beta}$), p is the pressure, n is the unit normal vector of the surface, and ( ),$_\beta$ stands for the derivative with respect to the coordinate $\xi^\beta$.

The membrane equilibrium problem has the remarkable property of static determinacy: the wall stress depends on the load and the deformed geometry. For a fully convex membrane with known deformed geometry, Equation (18) furnishes three partial differential equations that suffice to determine the three components of the stress tensor in a Neumann boundary value problem. In other words, the wall stress in this case is completely independent of material models. For a deep membrane, even if clamped boundary or other displacement boundary conditions present, the influence of material behavior exists only in a thin boundary layer.

In the inverse approach, the weak form is formulated directly on the given deformed configuration, hence, the method is expected to sharply capture this static determinacy in pressurized deep membranes. The stress in the deformed state is determined by means of finding a stress-free configuration under an assumed elasticity model. The stress free configuration so obtained corresponds to a kinematically compatible configuration which can be brought back to the given deformed configuration upon the application of the given load. It has been demonstrated that, for a clamped deep membrane, the wall stress in regions sufficiently distanced from the clamp boundary is practically independent of the material models chosen to perform the computation. Thus, the "static stress" can be effectively predicted despite the introduction of elasticity models and the ignorance of realistic elasticity parameters.

Briefly, the finite element formulation starts with the standard weak form:

$$F := \int_\Omega t^{\alpha\beta} g_\alpha \cdot \delta x_{,\beta}\, da - \int_{\partial\Omega_t} \bar{t} \cdot \delta x\, ds - \int_\Omega pn \cdot \delta x\, da = b\; 0, \qquad (19)$$

Where $\Omega$ is the current surface, $\Omega \partial_t$ is the boundary upon which the traction $\bar{t}$ is applied, and $\delta x$ is any kinematically admissible variation to the current configuration. In the finite element space the configurations and the variation are approximated by:

$$F := \int_\Omega t^{\alpha\beta} g_\alpha \cdot \delta x_{,\beta}\, da - \int_{\partial\Omega_t} \bar{t} \cdot \delta x\, ds - \int_\Omega pn \cdot \delta x\, da = 0, \qquad (20)$$

Here, the superscript I indicates the nodal number, Nel is the total number of nodes in the element, and $N_I$ is the shape function for the $I^{th}$ node. Introducing the matrix forms of stress and strain variables, the finite element equation may be written as:

$$\int_\Omega B^T t\, da - f^{ext} = 0, \qquad (21)$$

where B is the strain-displacement matrix and $f^{ext}$ is the external nodal force vector. In the inverse setting, the constitutive Equation (10) is regarded as a function of the referential metric tensor Gas, which in turn depends on the reference configuration via the relation $$G_{\alpha\beta} = \frac{\partial X}{\partial \xi^\alpha} \cdot \frac{\partial X}{\partial \xi^\beta}.$$

The FEM system therefore gives rise to a set of nonlinear algebraic equations for the nodal values of X. In our implementation, these nonlinear equations are solved iteratively using the Newton-Raphson procedure.

The idea of using inflation of membrane to determine the wall properties was not new. However, previous implementations were limited to axisymmetric membranes, for which the stress solution on any deformed configuration is available in closed-form. In this invention, the idea has been extended to membrane structures of general convex shape. The ability to compute the static stress in general membrane structures, albeit numerically, is a significant step forward in technology. It substantially expands the scope of early inflation tests.

The inverse method, however, has several limitations. The method does not apply to membranes that have flat or concave regions. If a membrane has a flat or nearly flat surface area, the ensuing finite element system becomes ill-conditioned or even singular, reflecting the fact that a flat membrane cannot sustain a transverse load. If the surface is concave, equilibrium requirement may render compressive wall stress which should be ruled out by stability consideration. Therefore, the inverse method is not a general method for membrane problems. Rather, it should be applied with discretion.

The inverse solution may not converge if the material model is not chosen properly. For example, if the material is too compliant, the ensuing reference configuration may revert the original surface curvature thus causing numerical difficulty. Nevertheless, stiffer material models often lead to converged solution. Once the solution converges, the stress depends minimally on the material parameters.

Figure 2:
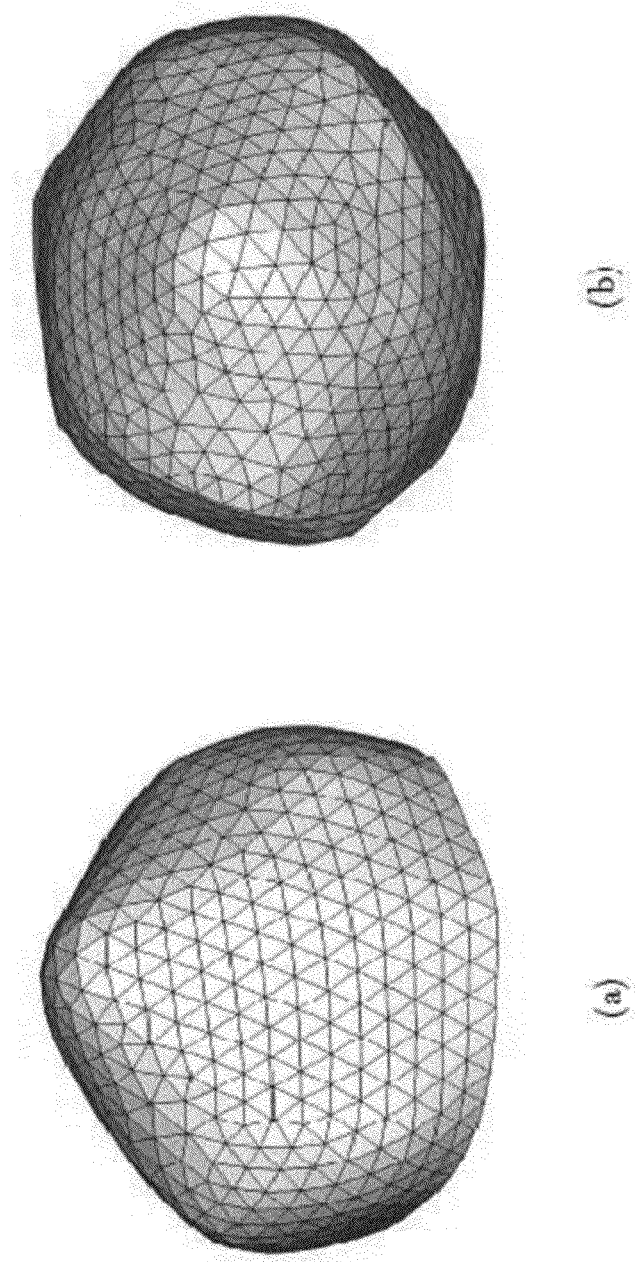
FIG. 2 illustrates an undeformed geometry and finite element mesh according to the present invention.

An experiment is simulated using a numerical model. FIG. 2 illustrates an undeformed geometry and finite element mesh. The mesh was originally constructed from the images of a cerebral aneurysm sac, which is convex but does not have any particular geometric symmetry. The wall is assumed to be described by the strain energy function $\omega_A = \mu^1$:

$$w_A = \frac{\mu_1}{2}(I_1 - 2\log J - 2) + \frac{\mu_2}{4}(I_1 - 2)^2, \qquad (22)$$

with:

$$\mu_1 = 0.06521739\ \text{N/mm},\ \mu_2 = 0.1521739\ \text{N/mm}. \qquad (23)$$

This embodiment is referred to herein as Model A. The parameters μ1 and μ2 are the multiplication of 3-D elasticity constants with a wall thickness. Parameters like these are referred to as effective elasticity constants. To simulate the clamped boundary constraint typically used in experiments, it is assumed that the base of the sac is fixed. Eleven deformed configurations are computed by applying pressures ranging from 60 to 110 mmHg with an interval of 5 mmHg. This is conducted using the forward nonlinear membrane element in a nonlinear finite element analysis program. The maximum surface stretch, which occurs at 110 mmHg pressure, is about 10%.

The generated deformed configurations are taken as input and the PWIM is applied to identify the elasticity parameters. The stress distribution in each configuration is computed by the inverse finite element method using a material model that has the same energy function as Model A, but 10 times elevated material constants. The stress is also computed using 100 times elevated parameters to assess the sensitivity of stress to material parameters.

Strain distributions in each configuration are computed with the aid of the finite element interpolation of Equation (20). Here, the surface inside an element is parameterized by the finite element natural coordinates. From the finite element interpolation of Equation (20):

$$g_\alpha = \sum_{I=1}^{Nel} \frac{\partial N_I}{\partial \xi^\alpha} x^I, \quad g_{\alpha\beta} = \sum_{I=1}^{Nel} \sum_{I=J}^{Nel} \frac{\partial N_I}{\partial \xi^\alpha} \frac{\partial N_J}{\partial \xi^\beta} x^I \cdot x^J. \quad (24)$$

When the global stress-free reference configuration is given, the quantities $G_\alpha$ and subsequently the deformation tensor C and its invariants $I_1$ and $I_2$ are computed accordingly.

As seen from Equation (11), the stress components are functions of the components of the reference and the current metric tensors, and the elasticity parameters appearing in the constitutive law. As described above, at every integration point in each of deformed configurations, the stresses and at least the convected components $g_{\alpha\beta}$ of the current metric tensor can be obtained. Choosing an appropriate constitutive model, the model stress is expressed as functions of the metric tensors and elasticity constants. The model stress in the i-th configuration is denoted by:

(25) where t stands for the set of elastic parameters and $(i)^t\alpha\beta$ is the experimental stress components obtained from the inverse analysis. A logical objective or cost function which represents the difference between the modeled and observed responses is:

$$^{(i)}t^{\alpha\beta} = t^{\alpha\beta}(\mu, {}^{(i)}g_{\delta\gamma}, G_{\delta\gamma}), \quad (26)$$

where, N is the total number of deformed states. In tensor notation, $\Phi = \Sigma_{i=1}^N \|{}^{(i)}t - {}^{(i)}\hat{t}\|^2$. If the global stress-free configuration is given, $\Phi$ is a function of the material parameters only. Otherwise, $\Phi$ depends also on the local metric tensor components $\mathcal{G}_{\alpha\beta}$, which will be included in the identification. This amounts to adding three additional model parameters to the optimization problem at every regression point. Since $\mathcal{G}$ is a metric tensor, it is natural to impose the positiveness requirement. In this case, the regression problem can be described as:

$$\text{minimize} \quad \Phi(\mu, \mathcal{G}_{\alpha\beta}) \quad (27)$$
$$\text{subject to} \quad \mathcal{G}_{11} > 0, \mathcal{G}_{22} > 0, \mathcal{G}_{11}\mathcal{G}_{22} - \mathcal{G}_{12}^2 > 0,$$
$$\text{and} \quad 1 \leq (\mu, \mathcal{G}_{\alpha\beta}) \leq u.$$

Here, l and u are the lower and upper bounds of the regression variables $\mu$ and $\mathcal{G}_{\alpha\beta}$. The parameter identification was performed by a gradient-based, sequential quadratic programming algorithm, known as SNOPT. As long as the constitutive model is selected, the analytical gradients of the objective function $\Phi$ with respect to the regression variables can be computed.

In order to validate the capability of the method, the obtained stress-strain data are fitted to two constitutive models; one is the same model as used in the process of generating the deformed configurations known as Model A, and the other is a distinct model referred to herein as Model B. Model B exhibits a similar mechanical behavior to that of Model A. Model B has the energy function:

$$w_B = v_1(\exp(I_1 - 2\log J - 2) - 1) + \frac{v_2}{4}(I_1 - 2)^2, \quad (28)$$

here $v_1$ and $v_2$ are effective elastic parameters. In the neighborhood of $(I_1, I_2)=(2, 1)$, the two energy functions obviously have similar characteristics. The parameter identification is performed under the assumptions of knowing the reference configuration and without knowing the reference configuration.

Figure 3:
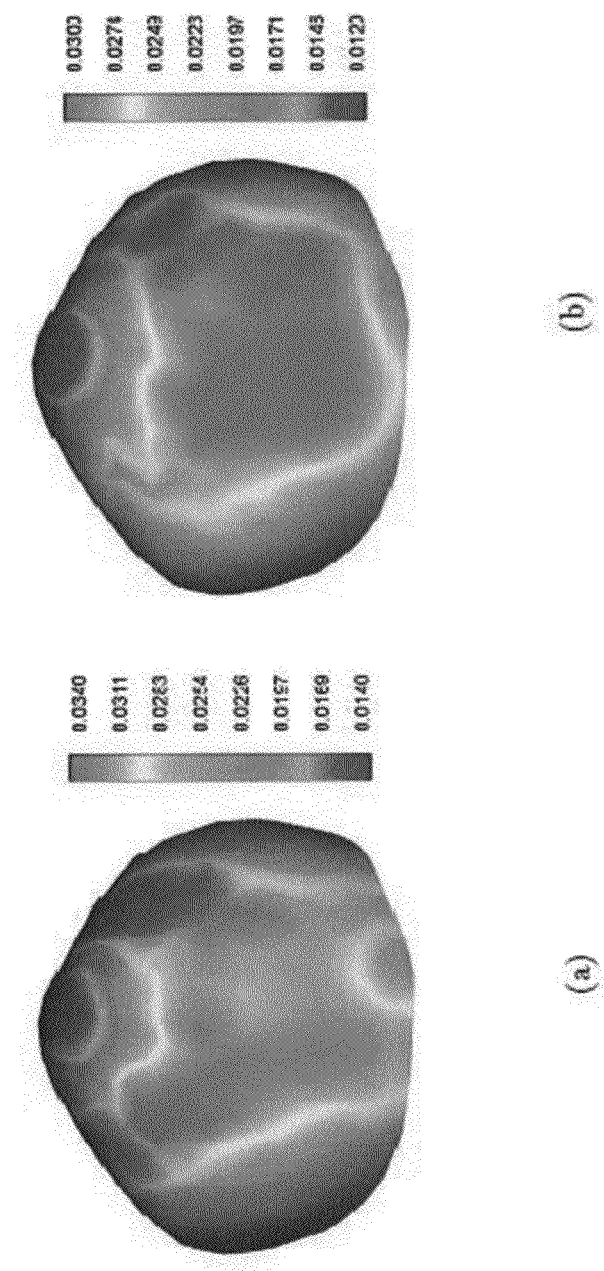
FIG. 3 illustrates the distribution of principal stress according to the present invention.
Figure 4:
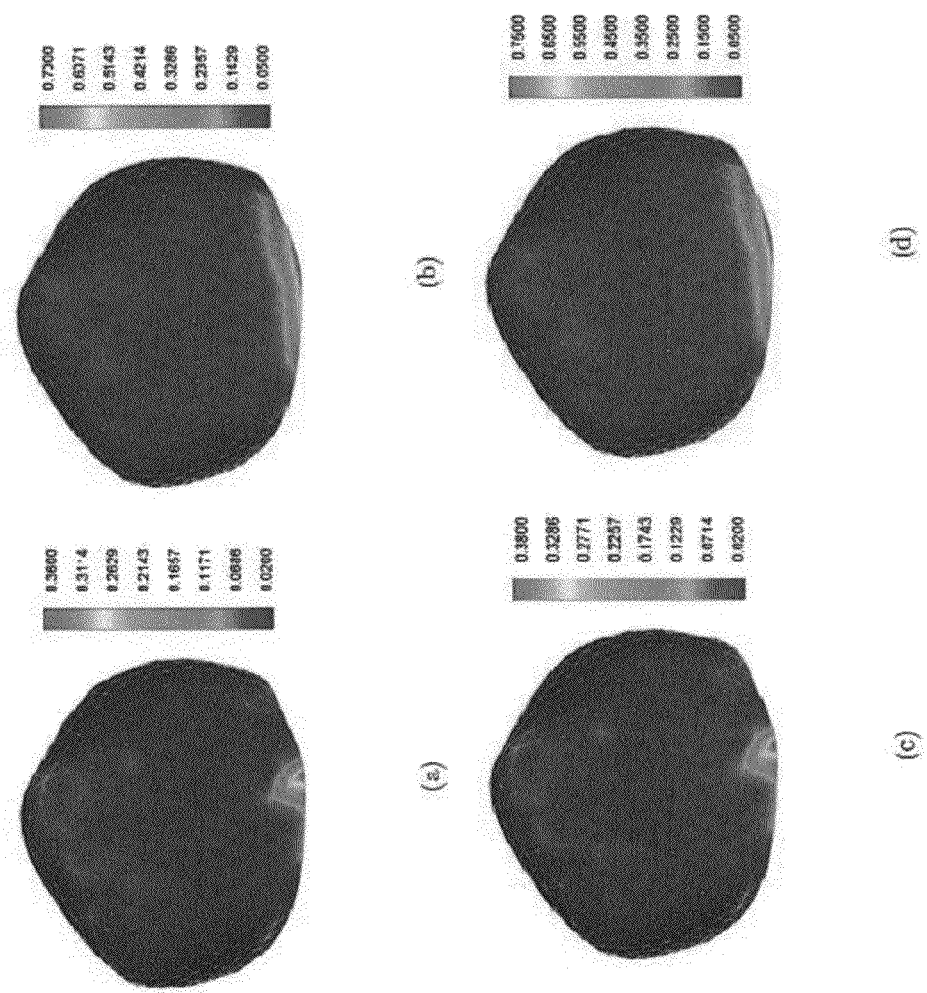
FIG. 4 illustrates the percentage difference in principal stresses under the change of elasticity parameters according to the present invention.

The distribution of the principal stresses predicted from Model A at the highest pressure (p=110 mmHg) is shown in FIG. 3. FIG. 4 shows the percentage difference in the principal stresses under drastic changes in elasticity parameters of Model A. The upper and lower rows show the percentage difference due to the increase of both material parameters µ1 and µ2 by 10 times and 100 times, respectively. Conservatively speaking, the change of the principal stresses is less than 0.15% in the region two layers of elements above the clamped base. In the region near the boundary, the change of principal stresses is relatively large. However, it is below 1%. This analysis identifies the boundary-effect-free regions where parameter identification is to likely yield reliable results. Later, the sac region excluding five layers of elements from the base is designated as the identification zone. The stress values computed from 10 times elevated parameters are used in the parameter regression.

Figure 5:
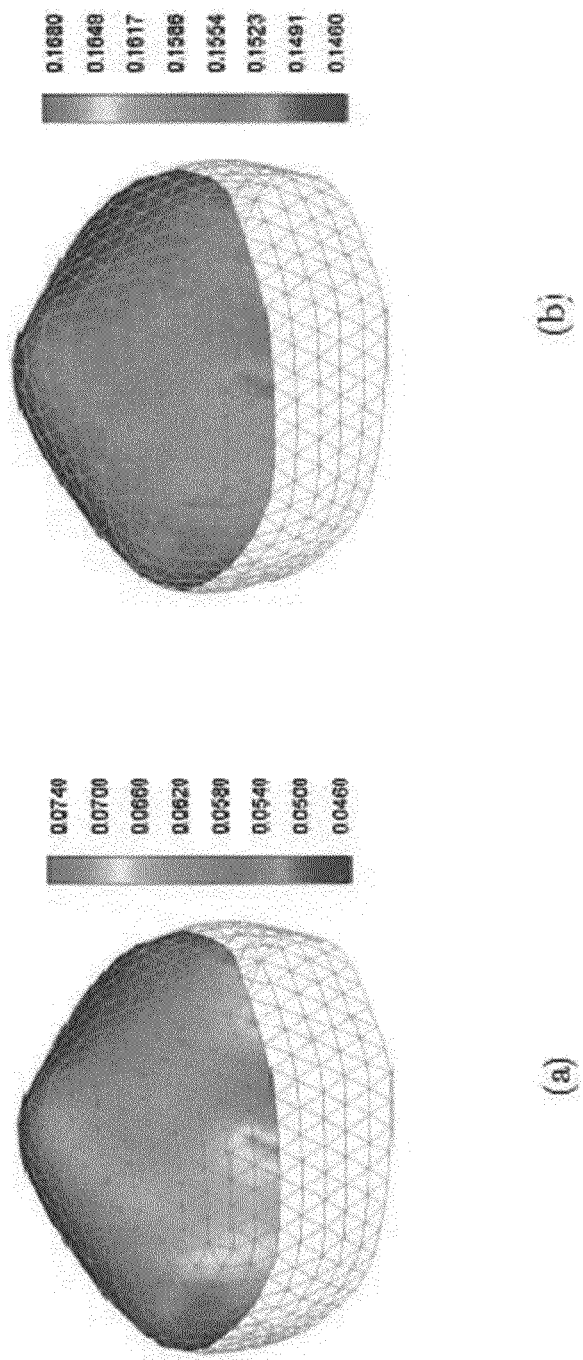
FIG. 5 illustrates identified elasticity parameters where the reference metric is known according to the present invention.
Figure 6:
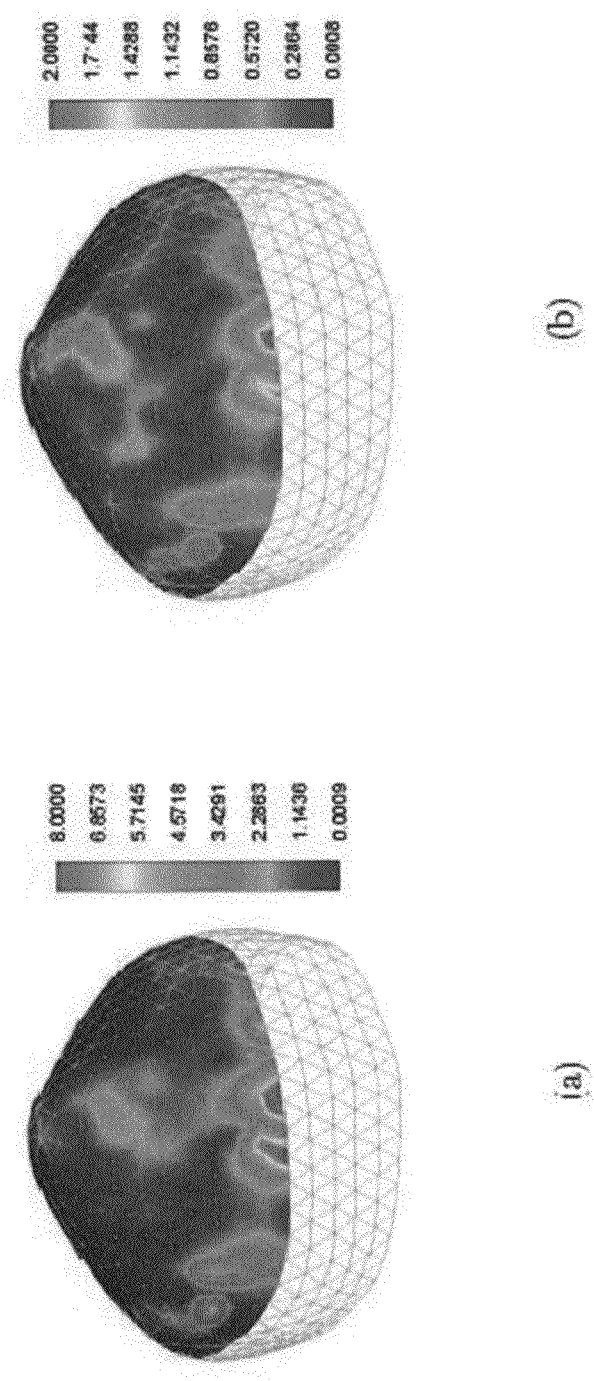
FIG. 6 illustrates absolute values of the relative error between identified elasticity parameters and true parameters where the reference metric is known according to the present invention.

FIG. 5 shows the distribution of the identified elasticity parameters ($\mu_1$ and $\mu_2$) of Model A under the condition that the global stress free-configuration is known. In this case, the original mesh is taken to be the reference configuration $\mathcal{C}_0$, and the referential quantities $G_{\alpha\beta}$ are computed from this given geometry. In the dome region six layers above the boundary which is shown in FIG. 5, the identified parameters $\mu_1$ ranges from 0.06119 N/mm to 0.07010 N/mm, and $\mu_2$ shows a narrower range of 0.14986 N/mm to 0.15410 N/mm. Since the stress is computed by FEIEM using a model different from that in the forward computation (10 times of the true elasticity parameters), and hence the acquired stress is not identical to the true stress, the identified parameters are expected to deviate from their true values. The distribution of the identification error (in percentage relative to the true parameters) by knowing the reference metrics are illustrated in FIG. 6. As the figures show, the identification error falls below 8% and 2% for $\mu_1$ and $\mu_2$, respectively.

Figure 7:
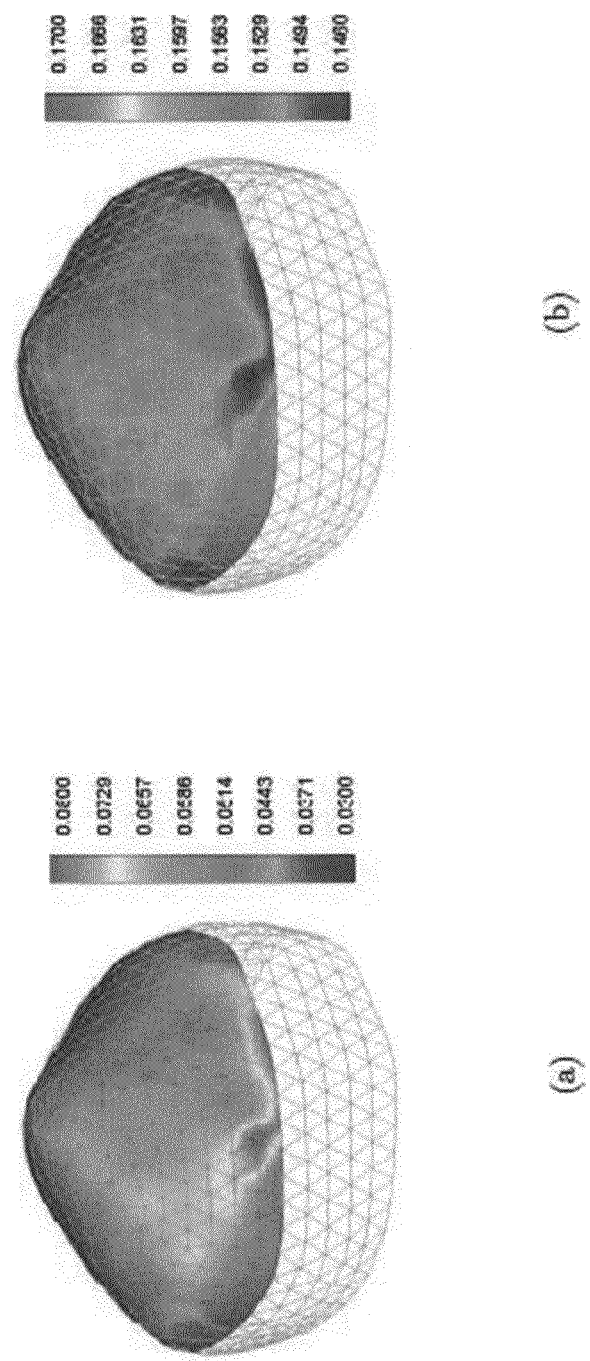
FIG. 7 illustrates identified elasticity parameters where the reference metric is not known according to the present invention.
Figure 8:
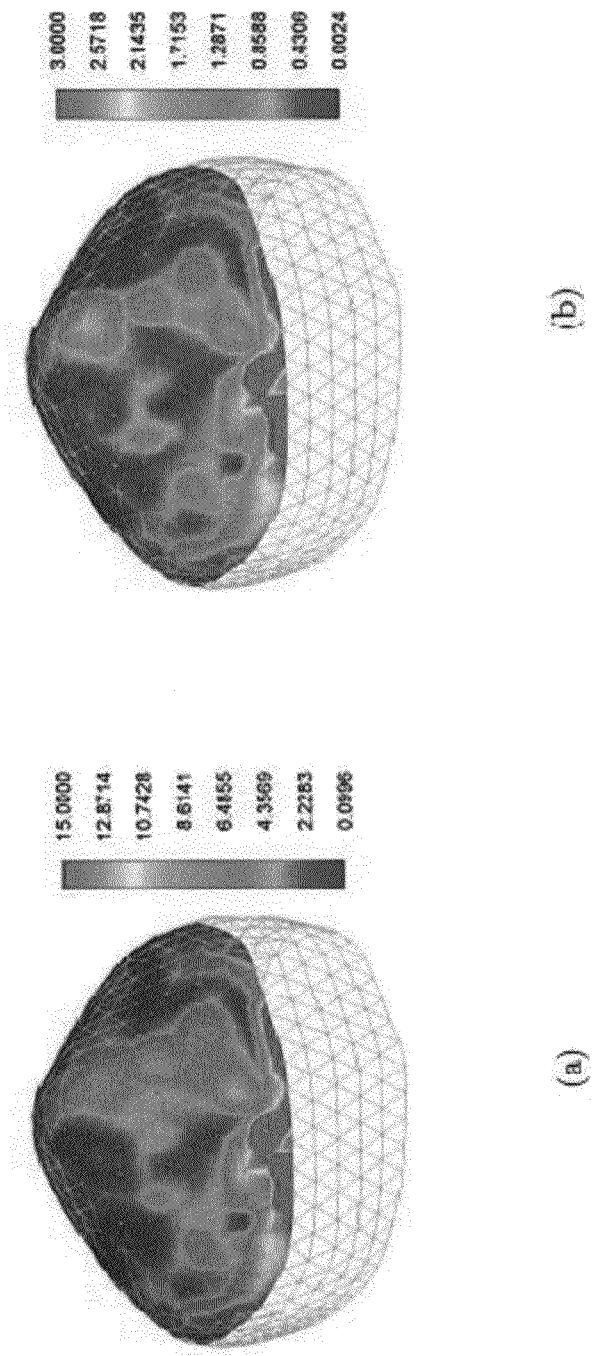
FIG. 8 illustrates absolute values of the relative error between identified elasticity parameters and true parameters where the reference metric is not known according to the present invention.

FIG. 7 illustrates the distribution of the identified elasticity parameters of Model A without the assumption of known stress-free configuration. FIG. 8 shows the identification error. In the dome region seven layers of elements away from the boundary, the identified parameters $\mu_1$ ranges from 0.05720 N/mm to 0.07872 N/mm, and $\mu_2$ presents a narrower range of 0.14647 N/mm to 0.15563 N/mm. The percentage error of the identified parameters falls below 15% and 3% for $\mu_1$ and $\mu_2$, respectively. It is evident that, in both cases the constant $\mu_2$, which is the leading parameter in this model, is recovered to within a very small error. The identification of constant $\mu_1$ is less accurate, but is still within an acceptable range.

Figure 9:
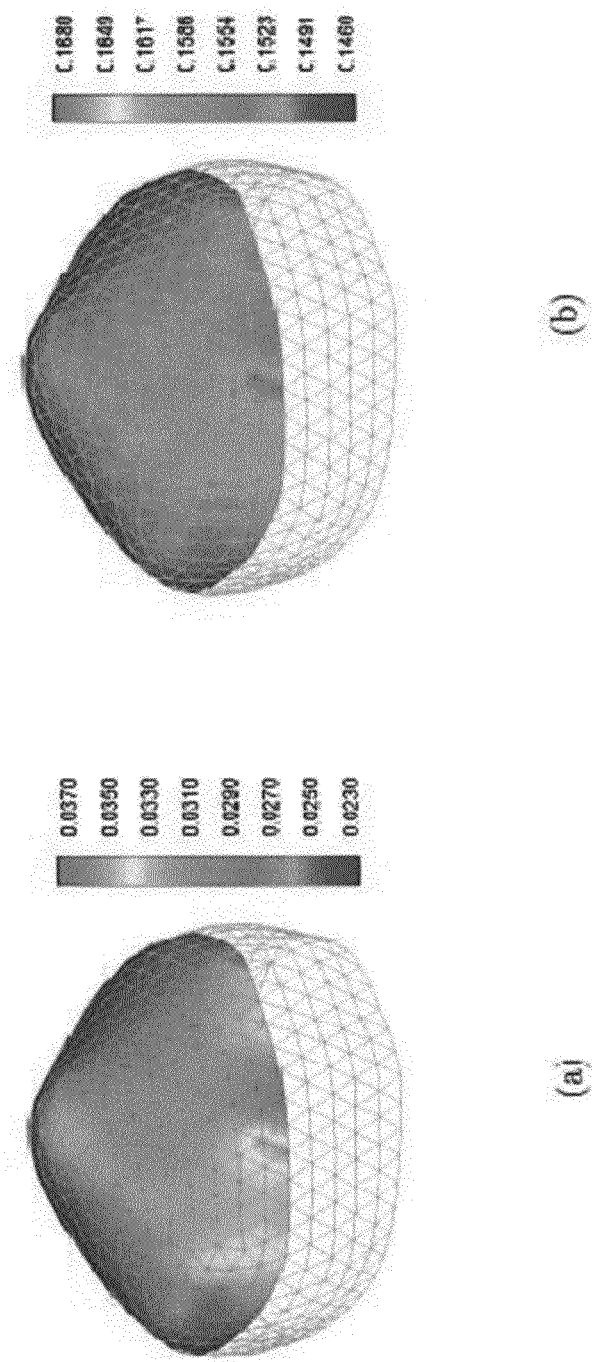
FIG. 9 illustrates identified elasticity parameters where the reference metric is known according to the present invention.
Figure 10:
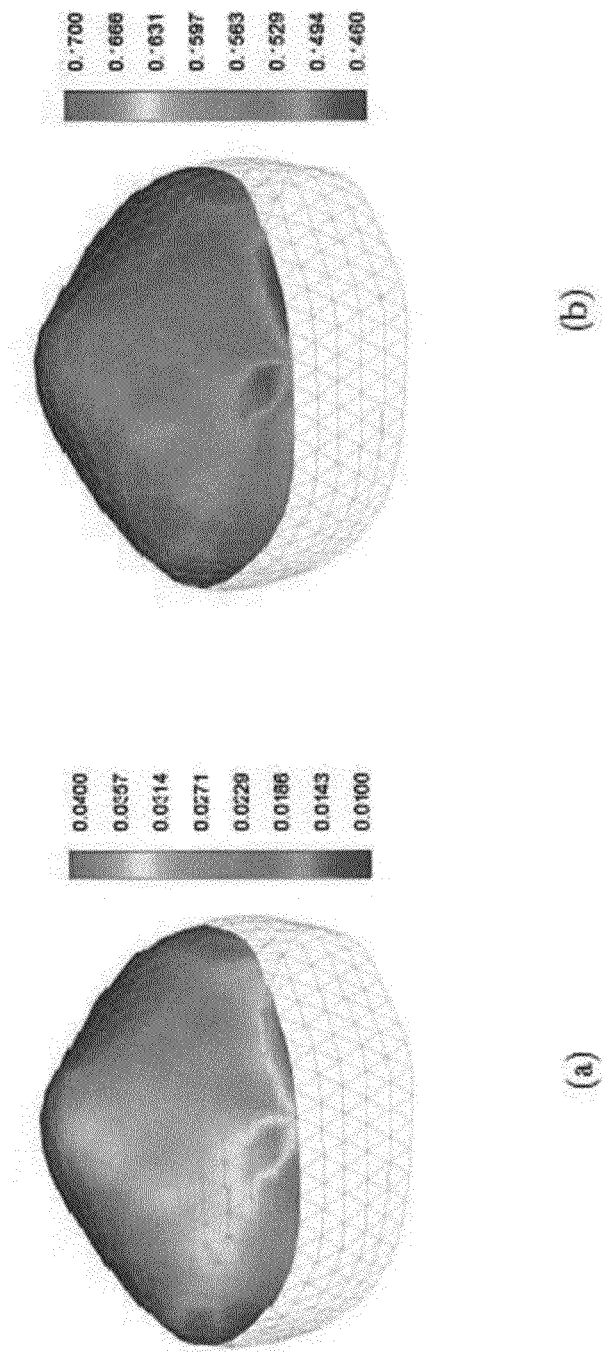
FIG. 10 illustrates identified elasticity parameters where the reference metric is not known according to the present invention.

FIG. 9 shows the distribution of the identified elasticity parameters of Model B, with the assumption of the stress-free configuration being given. The distribution of the parameters shows an approximate uniformity in the region six layers of elements away from the boundary. The ranges of the identified parameters are 0.03052 N/mm$\leq v_1 \leq$0.03492 N/mm, and 0.14981 N/mm$\leq v_2 \leq$0.15407 N/mm. FIG. 10 shows the distribution of the identified elasticity parameters of Model B, without assuming that the stress-free configuration is given. The distribution of the parameters is approximately uniform in the region seven layers of elements above the boundary. The ranges of the identified parameters are 0.02778 N/mm$\leq v_1 \leq$0.04037 N/mm, and 0.14524 N/mm$\leq v_2 \leq$0.15555 N/mm. It is expected that the identified parameters span wider ranges for the case of stress-free configuration being unknown due to the increase of the number of the regression variables.

It is also informative to conduct a statistical analysis in the boundary-effect-free region to examine how well the homogeneity has been identified. Table 1 and Table 2 list the means and standard deviations of the identified elasticity parameters for both models over the aforementioned boundary-effect-free regions for both knowing and without knowing the local stress-free configurations. For both models, adding the local reference metric tensor components as three more regression variables generally renders larger standard deviations of identified elasticity parameters. However, the standard deviations of these data, especially those of $\mu_2$ and $\nu_2$, are very small. Hence, it can be concluded that quantitatively the material homogeneity is satisfactorily recovered.

TABLE 1

The means and standard deviations of identified elasticity parameters of Model A and Model B knowing the reference metric tensor.

|  | Model A | | Model B | |
| --- | --- | --- | --- | --- |
|  | $\mu_1$ | $\mu_2$ | $\nu_1$ | $\nu_2$ |
| Mean (N/mm) | 0.06516 | 0.15208 | 0.03239 | 0.15206 |
| SD (N/mm) | 0.00113 | 0.00061 | 0.00057 | 0.00061 |

TABLE 2

The means and standard deviations of identified elasticity parameters of Model A and Model B without knowing the reference metric tensor.

|  | Model A | | Model B | |
| --- | --- | --- | --- | --- |
|  | $\mu_1$ | $\mu_2$ | $\nu_1$ | $\nu_2$ |
| Mean (N/mm) | 0.06484 | 0.15218 | 0.03132 | 0.15257 |
| SD (N/mm) | 0.00328 | 0.00143 | 0.00200 | 0.00168 |

Figure 11:
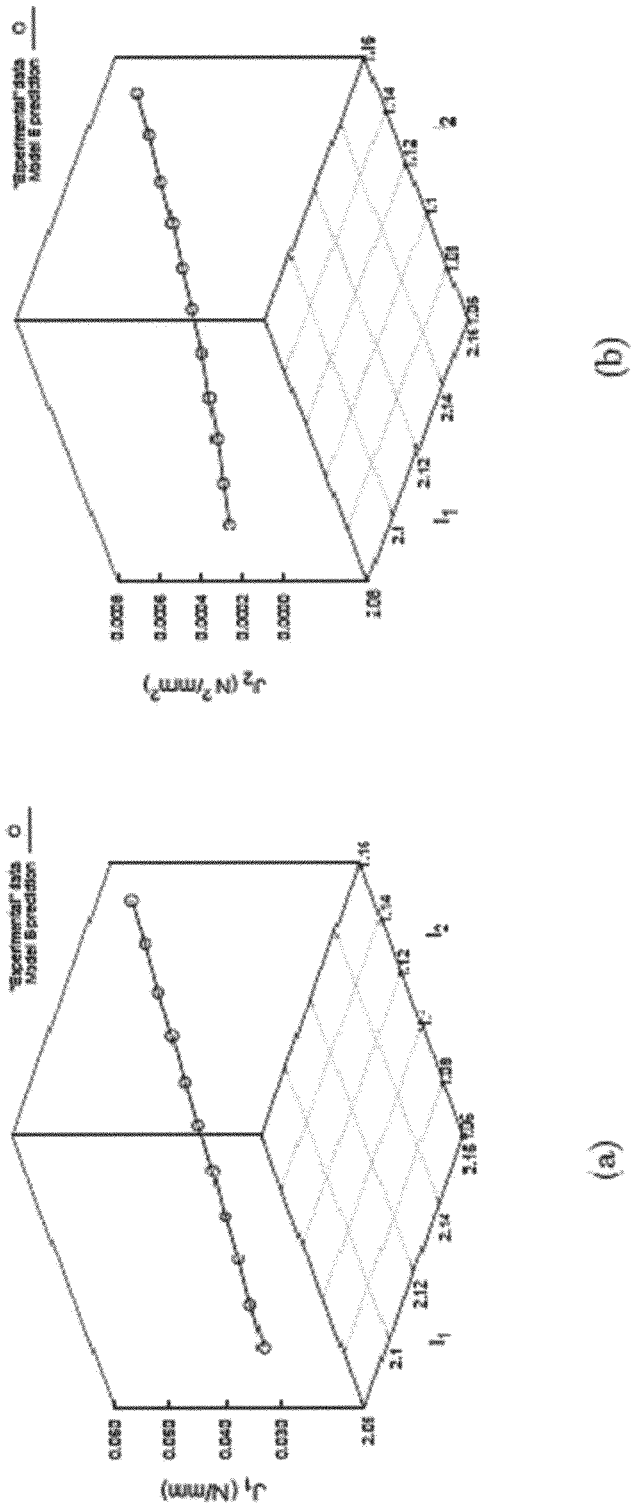
FIG. 11 is a graphical illustration of the comparison between the experimental stress invariants and the predicted stress invariants according to the present invention.

FIG. 11 illustrates the comparison between the stress invariants modeled by Model B and the experimental stress invariants at a point where a relatively large principal stretch ($\lambda_1$=1.076) occurs. The good match between these two curves suggests that Model B fits well with the stress-strain data generated by Model A.

Now, the pointwise membrane identification method (PWIM) for characterizing the distributive elastic properties in hyperelastic membranes is performed on a physical rubber balloon to validate the method.

Figure 12:
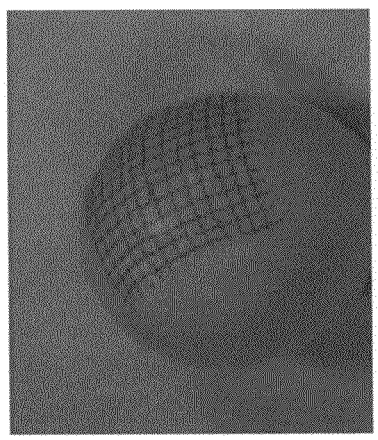
FIG. 12 is a photograph of a rubber balloon used in the process of three-dimensional geometry reconstruction according to the present invention.

A finite element mesh which constitutes 12×12 four-node elements was drawn by hand using a fine marker pen on the belly region of the balloon surface as shown in FIG. 12. Compressed nitrogen gas was used to inflate the balloon. Before testing, the rubber balloon underwent cyclical inflation-deflation preconditioning to eliminate the Mullin's effect. The Mullin's effect is strain induced stress softening in rubber material. Subsequently, the balloon is inflated to a relative large size of approximately 200% stretch. After several seconds waiting for the balloon to reach its stable status, the balloon is deflated in several decrements. At each state, the air pressure inside the balloon is measured using a manometer. In the meantime, four photos are taken from different perspectives using a calibrated camera. Since the balloon generally collapses when the net internal pressure is zero, the configuration under a very small pressure (0.0001 N/mm2), but still in convex shape, is taken as the approximate stress-free configuration. Fourteen configurations, including the stress-free configuration and thirteen deformed configurations, are recorded.

The deformed meshes in the deformed configurations are extracted using photogrammetry technique. Photogrammetry encompasses methods of image interpretation in order to derive the shape and location of an object from one or more photographs of that object. A primary purpose of photogrammetric measurement is the three dimensional reconstruction of an object in digital form. Photogrammetry works by first, calibrating a camera, which allows the photogrammetry program to know the detailed description of the camera, including the focal length, imaging scale, image center and lens distortion. Second, a sufficient number of photographs are taken of the object from different perspectives to sufficiently characterize its 3-D structure. Third, the photographs are imported into the program, and point referencing is then performed to let the program know the corresponding positions in each 2D image space of a point in the 3-D space. Finally, the 3-D position of all the selected points is computed using mathematical transformation. If applied to a deforming membrane with enough tracking markers on its surface, which sufficiently characterize the geometry feature of membrane, photogrammetry can be used to record the 3-D positions of the tracking markers in different deformed states. By identifying a reference configuration, a user can obtain the displacements of the tracking markers, and hence compute the strains using interpolation.

Taking the photos as input, a close-range photogrammetry program (Photo-Modeler 6 by EOS Systems Inc.) is used, to reconstruct the 3-D surface geometry of the meshed region in each configuration. In the process of 3-D geometry reconstruction, the point-to-point correspondence between the tracking points in different photographs is determined. Due to the difficulty in corresponding the nodes across different photographs automatically, the point-to-point correspondence may be determined manually such as by picking the points using mouse.

Taking the reconstructed finite element mesh of each deformed configuration, the wall tension using the membrane finite element inverse elastostatic method is computed individually. The inverse method leverages the material-insensitive nature of the stress in membrane structures, which enables computation of the wall stress using assumed material models. In this embodiment, a neo-Hookean type hyperelastic constitutive model is employed, where the strain-energy function is:

$$w_{neo-Hookean} = \frac{\mu_1}{2}(I_1 - 2\log J - 2) + \frac{\mu_2}{4}(I_1 - 2)^2. \quad (29)$$

Here, $I_1$=tr(C) and J=$\sqrt{\det(C)}$ where C is the right Cauchy-Green deformation tensor, and ($\mu_1, \mu_2$) are the effective elastic parameters. Without the second term, the energy function corresponds to the classical neo-Hookean material, which is known to suffer a limit-point instability during inflation motions. The second term is introduced as a remedy to stabilize the deformation. For the sake of quick convergence, unrealistic values of the elasticity parameters, $\mu_1=\mu_2=100$ N/mm which rendered a very small deformation, are assumed.

Clamped boundary conditions are applied on the four edges of the mesh. Clamped boundary or other types of displacement constraints compromises the stress static determinacy. However, for sufficiently curved membranes the influence exists in a thin boundary layer and the thickness of which depends inversely on the surface curvature. Outside the boundary layer, the stress is asymptotic to the static solution. It is hypothesized that the boundary layer can be identified numerically by examining the change of stress under varying material parameters. As mentioned above, the region in which the stress remains approximately invariant under relatively large change of material parameters is defined as the boundary-effect-free region. Eventually, the parameter identification is carried out in the boundary-effect-free region only. This procedure is important to the experiment design, since a practical method to eliminate the influence of boundary effect is needed.

The Cauchy tension tensor t and the referential tension tensor t are the resultants of the Cauchy stress $\sigma$ and the second Piola-Kirchhoff stress S, respectively:

$$t = h\sigma, \quad T = HS. \tag{30}$$

Here, h and H are the current and initial membrane thicknesses which are related through $h = \lambda_3 H$, where $\lambda_3$ is the thickness stretch. Relative to a convected basis, the tension tensors have the form:

$$t = t^{\alpha\beta} g_\alpha \otimes g_\beta, \quad T = T^{\alpha\beta} G_\alpha \otimes G_\beta. \tag{31}$$

The current basis $g_\alpha$ is related to the reference basis $G_\alpha$ pointwise through the relation $g_\alpha = F G_\alpha$ where F is the deformation gradient. It follows that the components of the tension and the referential tension differ only by the area stretch factor J, such as $T^{\alpha\beta} = J t^{\alpha\beta}$.

In the inverse computation the tension t is computed at each Gauss point in a local orthonormal coordinate system, and thus the outputs are the physical components which are denoted as $t_{11}, t_{22}, t_{12} = t_{21}$. The principal tensions, which will be used in parameter regression, can be directly computed according to:

$$t_1 = \frac{t_{11} + t_{22}}{2} + \frac{\sqrt{(t_{11} - t_{22})^2 + 4t_{12}^2}}{2}, \tag{32}$$

$$t_2 = \frac{t_{11} + t_{22}}{2} - \frac{\sqrt{(t_{11} - t_{22})^2 + 4t_{12}^2}}{2}.$$

However, the basis vectors defined independently in each configuration do not form a convected basis. The convected components of the stress can be computed through a linear transformation. Letting $\{\bar{g}_\alpha = 1, 2\}$ be a set of basis vectors at a point, and letting $\{g_\alpha = 1, 2\}$ be the convected basis at the same point, the tension tensor t is written in terms of the two sets of basis by:

$$t^{\alpha\beta} g_\alpha \otimes g_\beta = \bar{t}^{\alpha\beta} \bar{g}_\alpha \otimes \bar{g}_\beta. \tag{33}$$

Taking the dot product of both sides of Equation (33) with $g^+ \otimes g^\beta$ and letting $Q_\alpha{}^\beta = g^\beta \cdot \bar{g}_\alpha$, the following is obtained:

$$t^{\alpha\beta} = Q_\delta{}^\alpha \bar{t}^{\delta\gamma} Q_\gamma{}^\beta. \tag{34}$$

Based on the measured nodal positions in the reference and deformed configurations, the position vectors of a point inside the meshed region via the finite element interpolation are approximated:

$$X = \sum_{I=1}^{Nel} N_I(\xi^1, \xi^2) X^I, \quad x = \sum_{I=1}^{Nel} N_I(\xi^1, \xi^2) x^I. \tag{35}$$

Here, the superscript I indicates the nodal number, Nel is the total number of nodes in the element, and $N_I$ is the shape function for the $I^{th}$ node. The natural coordinates ($\xi^1, \xi^2$) serve as the element-wise convected surface coordinates. The displacement field is $u = x - X$. The covariant basis vectors of the reference and current configuration are computed respectively as:

$$G_\alpha = \frac{\partial X}{\partial \xi^\alpha} = \sum_{I=1}^{Nel} \frac{\partial N_I}{\partial \xi^\alpha} X^I, \quad g_\alpha = \frac{\partial x}{\partial \xi^\alpha} = \sum_{I=1}^{Nel} \frac{\partial N_I}{\partial \xi^\alpha} x^I. \tag{36}$$

The components of the covariant metric tensors on the reference and current surface, respectively, are given by:

$$G_{\alpha\beta} = G_\alpha \cdot G_\beta, \quad g_{\alpha\beta} = g_\alpha \cdot g_\beta. \tag{37}$$

Other geometric entities such as the contravariant basis vectors ($g^\alpha$, $G^\alpha$) and the contravariant metric tensor components ($g^{\alpha\beta}$, $G^{\alpha\beta}$) are computed. Subsequently, the deformation gradient F and the right Cauchy-Green deformation tensor $C = F^T F$ are computed at every Gauss point, with the deformation gradient $F = g_\alpha \otimes G^\alpha$ and $C = g_{\alpha\beta} G^\alpha \otimes G^\beta$. In this embodiment, a local orthonormal basis is constructed at every Gauss point in the reference configuration, rendering $G_{\alpha\beta} = \delta_{\alpha\beta}$ and $G^{\alpha\beta} = \delta^{\alpha\beta}$. The components of C with respect to this basis are the physical components.

The principal stretches $\lambda_1$ and $\lambda_2$ of the membrane are defined as the eigenvalues of the right stretch tensor U, which is related to the right Cauchy-Green deformation tensor C through $C = U^2$. Thus, the square stretches $\lambda_1^2$ and $\lambda_2^2$ are the eigenvalues of C, which are given, in terms of the physical components of C, by:

$$\lambda_1^2 = \frac{C_{11} + C_{22}}{2} + \frac{\sqrt{(C_{11} - C_{22})^2 + 4C_{12}^2}}{2}, \tag{38}$$

$$\lambda_2^2 = \frac{C_{11} + C_{22}}{2} - \frac{\sqrt{(C_{11} - C_{22})^2 + 4C_{12}^2}}{2}.$$

For materials in some symmetry classes, the stress function should satisfy certain universal relations. The universal relations are important in determining whether a material belongs to a certain symmetry class. For isotropic elastic materials, the relation:

$$SC = CS \tag{39}$$

holds, which implies that the second Piola-Kirchhoff stress tensor S commutes with the right Cauchy-Green deformation tensor C in every possible motion. Giving the linear relation between S and referential tension T, it is clear that T must satisfy:

$$TC = CT. \tag{40}$$

This is the universal relation for isotropic membranes.

Utilizing the acquired tension-strain data, it is examined whether TC=CT holds. Due to the experimental error, TC−CT will not be exactly zero even if the material is truly isotropic. The commutator e=TC−CT is employed as an indicator for isotropy. Due to the symmetry of T and C, the components $e_{11} = e_{22} = 0$, and the only possible non-zero component is $e_{12}$. The function $$\varepsilon = \frac{|2e_{12}|}{\|TC\|} \times 100$$

is introduced as a measure of co-axiality. If $\varepsilon$ is close to zero for a wide range of stress-strain protocols, the universal relation is satisfied. It should be noted that the test alone cannot conclude material isotropy, especially if only limited stress-strain protocols are tested. However, if the universal relation is found to hold true for a rich family of stress-strain protocols, then there is a strong justification to model the material as isotropic.

The mechanics of rubber elasticity has been investigated extensively in the last several decades, and various constitutive models have been developed. Among the well-known hyperelastic descriptors, there are mainly two types of energy functions, one in terms of the strain invariants and the other in principal stretches. Attributing to the limited extensibility of the molecule chain network, the stress-stretch curve shows a characteristic sigmoid shape. The experimental stress-stretch data displayed the same characteristic as that by Treloar. It has been well-accepted that the Ogden's energy function, which contains non-integer powers of the principal stretches, can model the sigmoid shape well within the typical range of experimental stretches. Based on this consideration, the Ogden model was selected to fit the experimental data.

The Ogden model describes the strain-energy function in terms of the principal stretches $\lambda_r$ (r=1, 2, 3), in the following form:

$$W = \sum_i \frac{M_i}{\alpha_i}(\lambda_1^{\alpha_i} + \lambda_2^{\alpha_i} + \lambda_3^{\alpha_i} - 3). \tag{41}$$

Here, W is the strain energy per unit reference volume, $M_i$ and $\alpha_i$ are elastic parameters. The exponent $\alpha_i$ may take any non-zero real value. The summation on i extends over as many terms as are necessary to characterize a particular material. For membranes, the strain energy per unit reference area is $\omega$=HW, where H is the reference membrane thickness. Hence, the 2D form of Equation (41) is:

$$w = \sum_i \frac{HM_i}{\alpha_i}(\lambda_1^{\alpha_i} + \lambda_2^{\alpha_i} + \lambda_3^{\alpha_i} - 3). \tag{42}$$

The effective elasticity parameters, are introduced, $\mu_i$=$HM_i$ (i=1, 2, 3), and Equation (42) is rewritten as:

$$w = \sum_i \frac{HM_i}{\alpha_i}(\lambda_1^{\alpha_i} + \lambda_2^{\alpha_i} + \lambda_3^{\alpha_i} - 3) \tag{43}$$

The incompressibility condition, $\lambda_1\lambda_2\lambda_3$=1, gives rise to $\lambda_3$=$(\lambda_1 \lambda_2)^{-1}$. Considering $\lambda_1$ and $\lambda_2$ two independent deformation parameters, Equation (43) may be rewritten as:

$$\hat{w}(\lambda_1, \lambda_2) = \sum_i \frac{\mu_i}{\alpha_i}(\lambda_1^{\alpha_i} + \lambda_2^{\alpha_i} + \lambda_1^{-\alpha_i}\lambda_2^{-\alpha_i} - 3). \tag{44}$$

It follows that under the plane stress assumption ($t_3$=0) the principal values of the tension tensor are given by:

$$t_1 = \frac{1}{\lambda_2}\frac{\partial \hat{w}}{\partial \lambda_1}, t_2 = \frac{1}{\lambda_1}\frac{\partial \hat{w}}{\partial \lambda_2}. \tag{45}$$

Expanding Equation (45):

$$t_1 = \sum_i \mu_i(\lambda_1^{\alpha_i-1}\lambda_2^{-1} - (\lambda_1\lambda_2)^{-\alpha_i-1}), \tag{46}$$

$$t_2 = \sum_i \mu_i(\lambda_2^{\alpha_i-1}\lambda_1^{-1} - (\lambda_1\lambda_2)^{-\alpha_i-1}).$$

It was shown by Ogden that the energy function shown by Equation (43) fits well the data of a particular rubber material by Treloar if three terms are included. Following this observation, the three-term Ogden model is chosen. The objective function is constructed as:

$$\Phi = \sum_{i=1}^{N} w_1({}^{(i)}t_1 - {}^{(i)}\hat{t}_1)^2 + w_2({}^{(i)}t_2 - {}^{(i)}\hat{t}_2)^2 \tag{47}$$

where, N is the number of deformed states recruited into the regression, ${}^{(i)}t_\alpha$ and ${}^{(i)}\hat{t}_\alpha$ ($\alpha$=1,2) are the model predicted and experimental principal tensions in the ith configuration, $\omega_1$ and $\omega_2$ are the weight parameters, the values of which are determined by numerical experiments. To achieve the reported results, $\omega_1$=1.0 and $\omega_2$=1.5 are chosen. Since an approximate global stress-free configuration was obtained, $\Phi$ is a function of the unknown elasticity parameters only. The parameter identification problem can be described as:

$$\text{minimize } \Phi(\mu, \alpha) \tag{48}$$
$$\text{subject to } 1 \leq (\mu, \alpha) \leq u.$$

Here, $(\mu, \alpha)$=$(\mu_1, \mu_2, \mu_3, \alpha_1, \alpha_2, \alpha_3)$ is the vector of elasticity parameters, l and u are the vectors of lower and upper bounds of $(\mu, \alpha)$.

A practical difficulty in material parameters identification is that multiple sets of parameters may render equally good fits to the given stress-strain data due to the presence of local minima or experimental error or regression error. The problem aggravates for highly nonlinear models for which a small perturbation in the experimental data may result in a drastic variation in the ensuing parameters. This issue has a non-trivial implication in membrane identifications. While the 3-D energy function parameters are intrinsic properties of the material, the effective properties in the membrane energy function such as $\mu_i$ in Equation (43) are not. Their values depend on the wall thickness, and thus may vary with the thickness even if the underlying material is intrinsically homogeneous. Due to the numerical non-uniqueness in fitting, a variation in the wall thickness may result in a spurious heterogeneity in the identified intrinsic parameters. To cope with this difficulty, regression is performed at a selected point where the response is relatively smooth and the parameters $\alpha_i$ and $\mu_i$ are determined. Then, based on the consideration that the balloon is approximately homogeneous, the values of $\alpha_i$ are applied to all other points and the remaining effective parameters $\mu_i$ are identified. Although the parameters obtained are unlikely the global minimizer of the objective function, the assumed material homogeneity is enforced. The regression is performed by a gradient-based, sequential quadratic programming (SQP) algorithm such as SNOPT.

The usefulness of the identified elastic parameters can be evaluated by examining how well the model derived from a set of experiments can predict the system behavior in a different physical setting. A forward finite element analysis is conducted using the identified model to predict a deformed configuration, which was not used in the parameter identification. The finite element method predictions are compared to the measured deformation. In the forward analysis, the finite element formulation of the Ogden model is followed for membrane problems. The element is implemented in a nonlinear finite element program such as FEAP.

The forward finite element analysis is conducted for the boundary-effect-free region where the parameter identification is carried out. The identified parameters $\alpha_i$ and the averages of the identified parameters $\mu_i$ over the region are input as the model parameters. The displacements of the boundary nodes were prescribed according to the recorded nodal positions. The difference between the predicted position x and measured position $\hat{x}$ is quantified node-wise with the error measure $$e = \frac{\|x - \hat{x}\|}{L},$$

where L is a characteristic length taken to be 50 cm.

Figure 13:
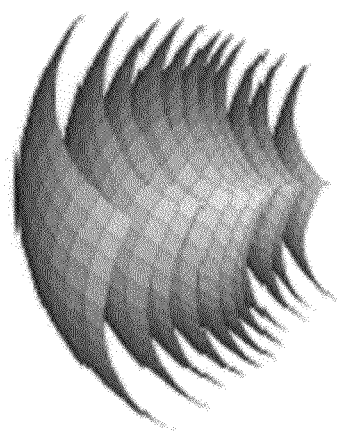
FIG. 13 illustrates reconstructed meshes of deformed configurations according to the present invention.

Table 3 lists the thirteen deformed configurations and their corresponding pressure values. As shown in Table 3, the largest stretch being around 2.1 occurred in the configuration 13, which is the highest pressure. The initial size of a randomly selected element in the stress-free configuration is about 5.3× 5.3 mm$^2$, whereas in the deformed configuration 13, its size is around 10.6×10.6 mm$^2$. FIG. 12 is a photograph of a rubber balloon used in the process of three-dimensional geometry reconstruction according to the present invention. FIG. 13 shows the reconstructed mesh for the deformed configurations. Two deformed configurations which were close to other ones are not shown. Qualitatively, the convexity and smoothness of membrane surfaces have been recovered.

TABLE 3

The identities and corresponding pressure values of the deformed configurations.

| Configuration ID | | | | | | |
|---|---|---|---|---|---|---|
| 1 | 2 | 3 | 4 | 5 | 6 | 7 |
| Pressure (N/mm$^2$) 0.00089 | 0.00134 | 0.00153 | 0.00161 | 0.00167 | 0.00173 | 0.00179 |

| Configuration ID | | | | | |
|---|---|---|---|---|---|
| 8 | 9 | 10 | 11 | 12 | 13 |
| Pressure (N/mm$^2$) 0.00184 | 0.00190 | 0.00198 | 0.00208 | 0.0022 | 0.00238 |

Figure 14:
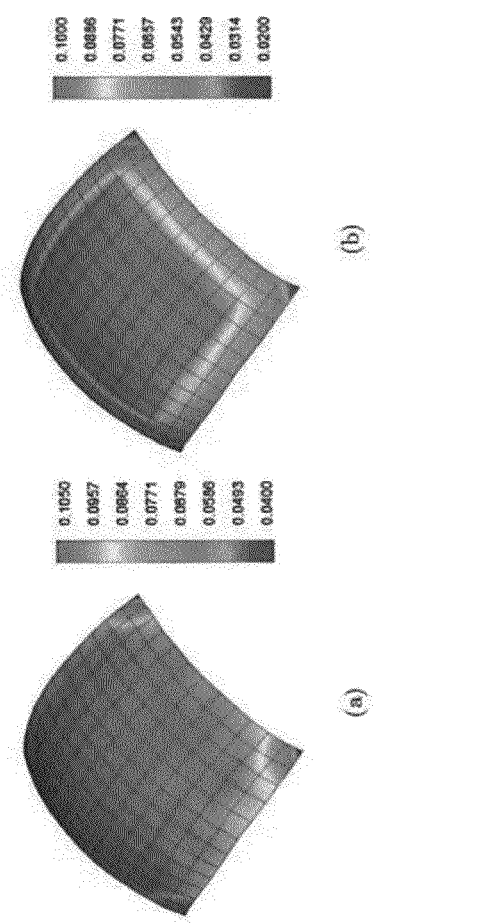
FIG. 14 illustrates distribution of principal tensions of deformed configurations according to the present invention.

FIG. 14 illustrates distribution of principal tensions of deformed configurations, specifically the principal tensions in the 13th state—the highest pressure. It should be noted that the stress solution obtained through FEIEM is largely affected by the geometric features of the surface, e.g. smoothness and curvature. Due to the unavoidable existence of experimental error, the reconstructed membrane surface may have some unphysical local undulations depending on the accuracy of the motion tracking devices. In that case, the stress solution may not converge, or has stress concentrations here and there. In order to reduce this artifact, it is imperative that certain surface smoothing processes be conducted prior to stress computation. According to this embodiment of the present invention, good quality surface meshes were obtained from 3-D reconstruction without modification for all the configurations.

Figure 15:
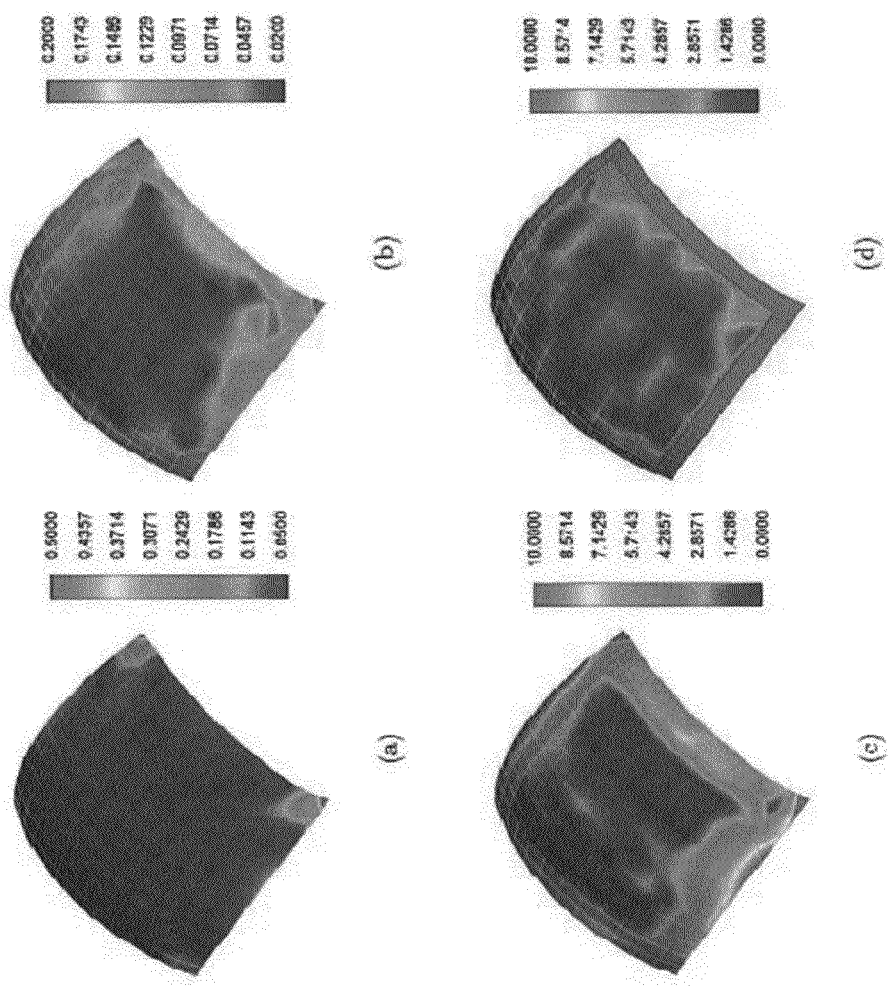
FIG. 15 illustrates the percentage difference of principal tensions under the change of elasticity parameters according to the present invention.

FIG. 15 illustrates the relative difference of the principal tensions under drastic changes in elasticity parameters of the neo-Hookean model. The parameters $\mu_1 = \mu_2 = 100$ N/mm are taken as the reference values. After varying the two parameters in different ways, the principal tensions using FEIEM were computed, and compared to the computed reference parameters. In FIG. 15, the upper row shows the percentage difference in principal stresses when both parameters were magnified 10 times, i.e., $\mu_1 = \mu_2 = 1000$ N/mm. The percentage differences in the region three layers of elements distanced from the boundary were below 0.05%. Increasing both parameters by 100 times produces a similar difference margin. In the lower row, $\mu_1$ was kept unchanged, while $\mu_2$ was increased to 5 times, or $\mu_1 = 100$ N/mm and $\mu_2 = 500$ N/mm. The percentage differences in the region three layers of elements distanced from the boundary were below 2.8%. The case where $\mu_1$ was increased to 5 times while $\mu_2$ remained unchanged was also considered and a similar margin of difference was observed.

Throughout all the tests, it appears that the tension solution was affected minimally by proportional variations of the elastic parameters. Changing two parameters unproportionally, however, rendered a relatively larger variation in the tension solution. Nevertheless, the difference was within an acceptable range in the region three layers of elements distanced from the boundary. This region was identified as the boundary-effect-region where the parameter identification was performed later.

Figure 16:
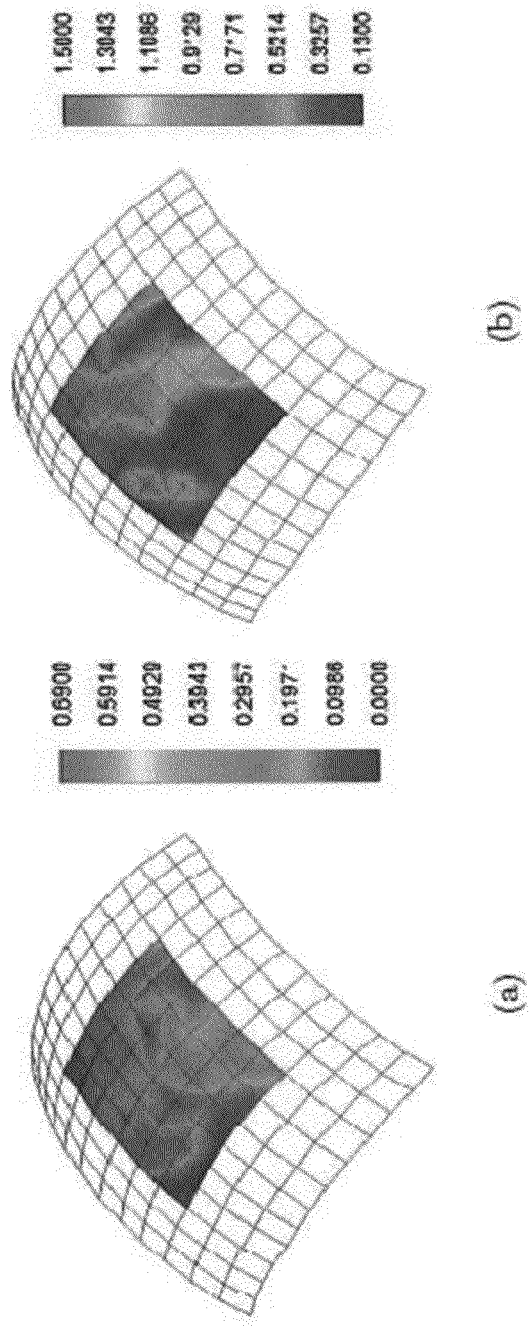
FIG. 16 illustrates the distribution of the co-axiality indicator in selected configurations according to the present invention.

FIG. 16 illustrates the distribution of the co-axiality indicator $\epsilon$ in the lowest and highest pressure states (configurations 1 and 13), respectively. In the boundary-effect-free region defined above, the value of was less than 0.58% and 1.07% for the configurations 1 and 13, respectively. The values in other states fall into these limits. Allowing for the experimental error, the co-axiality condition between the stress and strain tensors was met. Therefore, the rubber may be modeled as an isotropic material.

As previously discussed, the parameter identification was accomplished in two steps. First, the regression was performed at a selected Gauss point and all parameters were identified. Second, the identified $\alpha_i$ values were applied to the entire region, and the remaining parameters $\mu_i$ were identified at all remaining Gauss points. The identified values of $\alpha_i$ and $\mu_i$ at the selected point are listed in Table 4.

TABLE 4

The identified parameters $\alpha_i$ and $\mu_i$ for the Ogden model at a selected point.

| i | $\alpha_i$ | $\mu_i$ (N/mm) |
|---|---|---|
| 1 | 2.87181 | 0.05827 |
| 2 | −1.80776 | 0.01940 |
| 3 | −5.76831 | −8.477 × 10$^{-5}$ |

TABLE 5

Ranges, means, and standard deviations of the identified elasticity parameters.

|  | $\mu_1$ | $\mu_2$ | $\mu_3$ |
| --- | --- | --- | --- |
| Minimum (N/mm) | 0.05470 | 0.01473 | $-9.454 \times 10^{-5}$ |
| Maximum (N/mm) | 0.06453 | 0.02320 | $-6.221 \times 10^{-5}$ |
| Mean (N/mm) | 0.05986 | 0.01966 | $-8.154 \times 10^{-5}$ |
| SD (N/mm) | 0.00239 | 0.00171 | $6.923 \times 10^{-6}$ |

Figure 17:
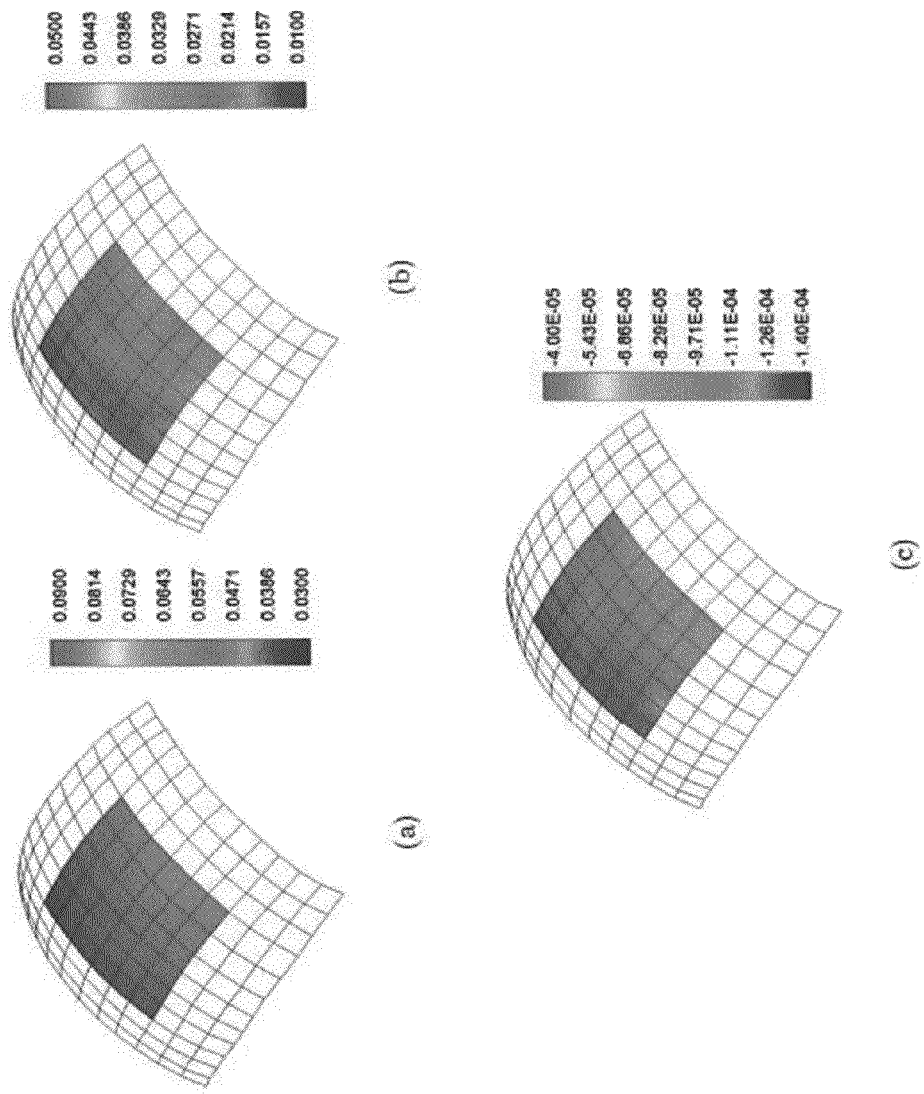
FIG. 17 illustrates identified elasticity parameters of the Ogden model according to the present invention.

The global regression was performed using the states in Table 5 excluding the 11th state (p=0.00208 N/mm$^2$), which was reserved for a forward verification. The distributions of the identified parameters $\mu_i$ in the whole region are shown in FIG. 17 for the boundary-effect-free region. The ranges, means, and standard deviations of these three parameters are listed in Table 5. Since the standard deviations for all the parameters are relatively small, it may be concluded that the material is at least nominally homogeneous.

Figure 18:
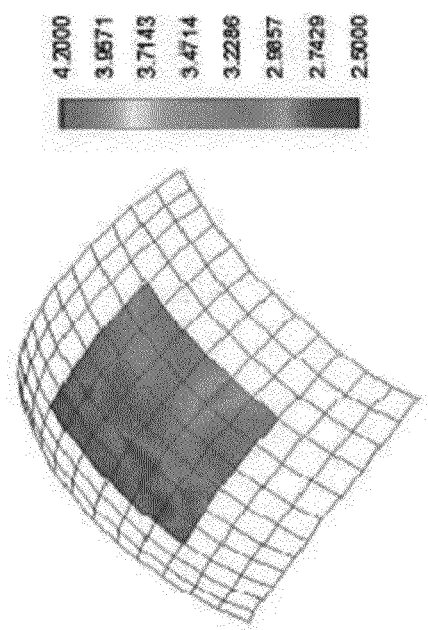
FIG. 18 illustrates a distribution of a ratio according to the present invention.

The intrinsical homogeneity of the material can be checked by inspecting the ratios, $$\frac{\mu 1}{\mu 2}, \frac{\mu 1}{\mu 3}, \text{ and } \frac{\mu 3}{\mu 2},$$

which factor out the wall thickness. Since $\mu_3$ is several orders of magnitude smaller than $\mu_1$ and $\mu_2$, only the ratio of $\mu_1$ to $\mu_2$ is examined. The distribution of this ratio is illustrated in FIG. 18. Qualitatively seen from FIG. 18, the ratio is approximately uniform over the region. The mean is 3.0309 N/mm, and the standard deviation is 0.1720 N/mm. The result suggests that the material is intrinsically homogeneous.

Figure 19:
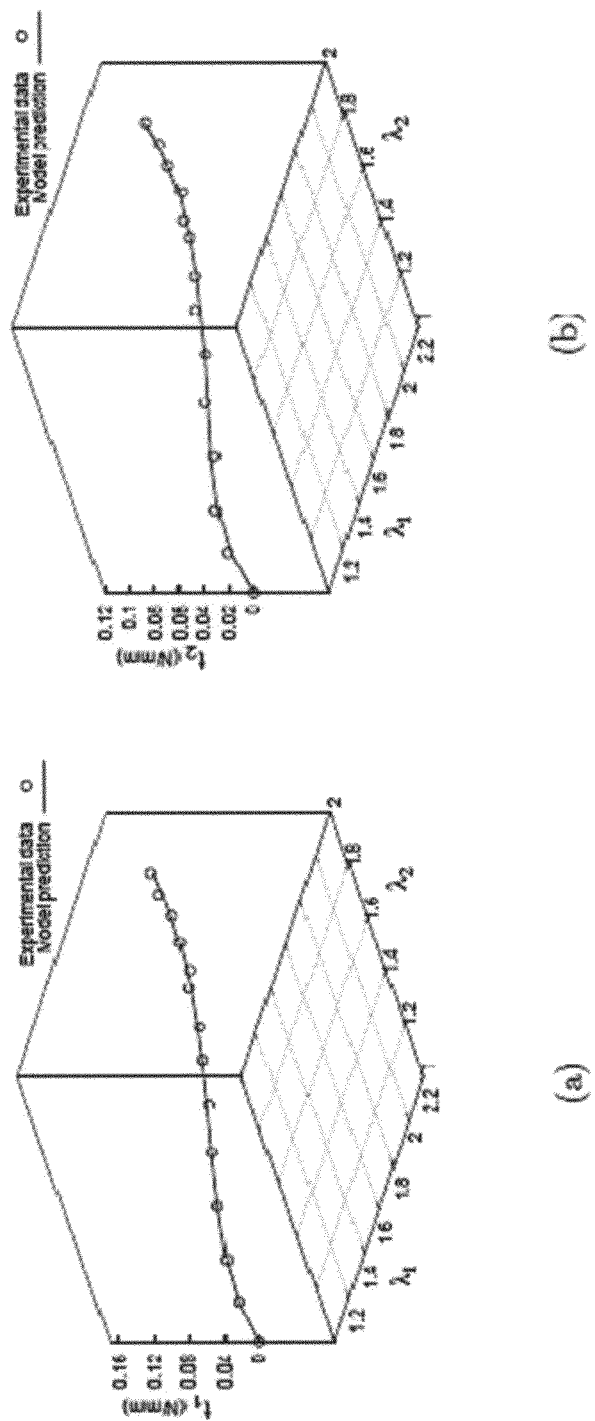
FIG. 19 is a graphical illustration of the comparison between the experimental tension curves and the model tension curves according to the present invention.

FIG. 19 is a graphical illustration of the comparison between the identified model's tension-stretch curves and the experimental data, at the point where the initial identification of all the six parameters took place. The match between the model-predictions and experimental data indicates that the material responses were modeled successfully by the Ogden model, at least within the stretch range considered in the experiment.

Figure 20:
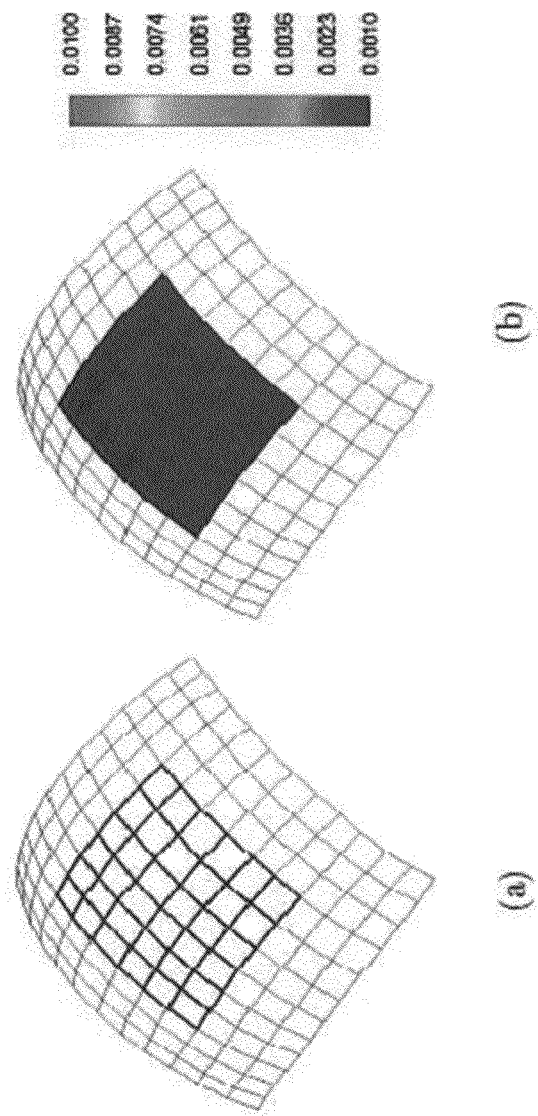
FIG. 20 illustrates a comparison between the deformed configuration computed from finite element method using the identified elastic parameters and the experimentally measured configuration according to the present invention.

The 11th configuration (p=0.00208 N/mm$^2$), which has been excluded from parameter identification, was recruited for a forward verification. FIG. 20 illustrates the comparison between the finite element predicted configuration using the identified mean elastic parameters and the experimentally measured configuration. In FIG. 20(*a*), the thick black mesh is the finite element prediction, and the thin gray mesh is the experimental result. The finite element analysis was performed for the boundary-effect-free region where the elastic parameter identification was conducted. Displacement boundary conditions corresponding to the measured nodal positions were applied along the boundary edges. FIG. 20(*b*) shows the distribution of the relative error between the predicted and measured nodal positions. As shown in the plots, the computed configuration coincides very well with the experimentally measured one. The position error $$e = \frac{\|x - \hat{x}\|}{L}$$

is less than 0.2% throughout the region.

The experimental method is designed for delineating the distributive elastic properties of membrane structures. Unlike the traditional specimen tests which rely on controlled homogeneous deformations, the present method does not require the uniformity of stress and strain in the allowable protocol. Instead, the actual stress and strain generated during a finite inflation motion of a membrane are employed to characterize the distributive properties. According to the present invention, it was verified experimentally that the method can effectively identify the membrane property and can recover the uniformity of parameters in a known homogeneous rubber balloon. The true value of the method, of course, lies in the potential of delineating the heterogeneous property distribution. So far, there is no effective experimental method that can sharply characterize heterogeneous materials.

An advantage of the present invention is its non-destructiveness. Due to the elimination of edge force measurement, the membrane does not need to be cut into pieces. The structure in its entirety is tested. Thus, the present invention provides a framework for designing non-invasive identification methods for thin biological tissues. When augmented with a suitable method for deformation data acquisition, the method may even lead to a non-invasive approach for extracting the in vivo elastic properties of thin living organs.

The accuracy of the method depends critically on the quality of stress and strain data. The former, in turn, is highly sensitive to the surface curvature and thus may be strongly influenced by the inaccurate characterization of the surface geometry. The ensuing surface quality for all configurations appeared to be acceptable. If a reconstructed surface has spurious local undulations, it may be necessary to smooth the surface prior to stress computation. Since the strain is computed from the nodal positions via interpolation, its quality is also affected by the aforementioned error. However, the influence on strain accuracy is much minor.

The issue of accuracy can be addressed from several avenues. The first possibility is to use accurate surface data acquisition techniques such as a laser scan. Commercial laser scanners can reconstruct solid surfaces to within sub-micron accuracy. The scanners often output triangulated surface or CAD models that can be readily meshed. Secondly, one may increase the mesh density by drawing more nodes on the surface. A finer mesh will capture the surface curvature better and produce more accurate stress results. As a by-product, it will also help sharpening the boundary layer identification. Alternatively, one may use high-order elements or other intrinsically smooth approximation methods such as the mesh-free methods or the isogeometric method. These methods are more accurate in geometric description, which in turn render more accurate stress solution.

Figure 21:
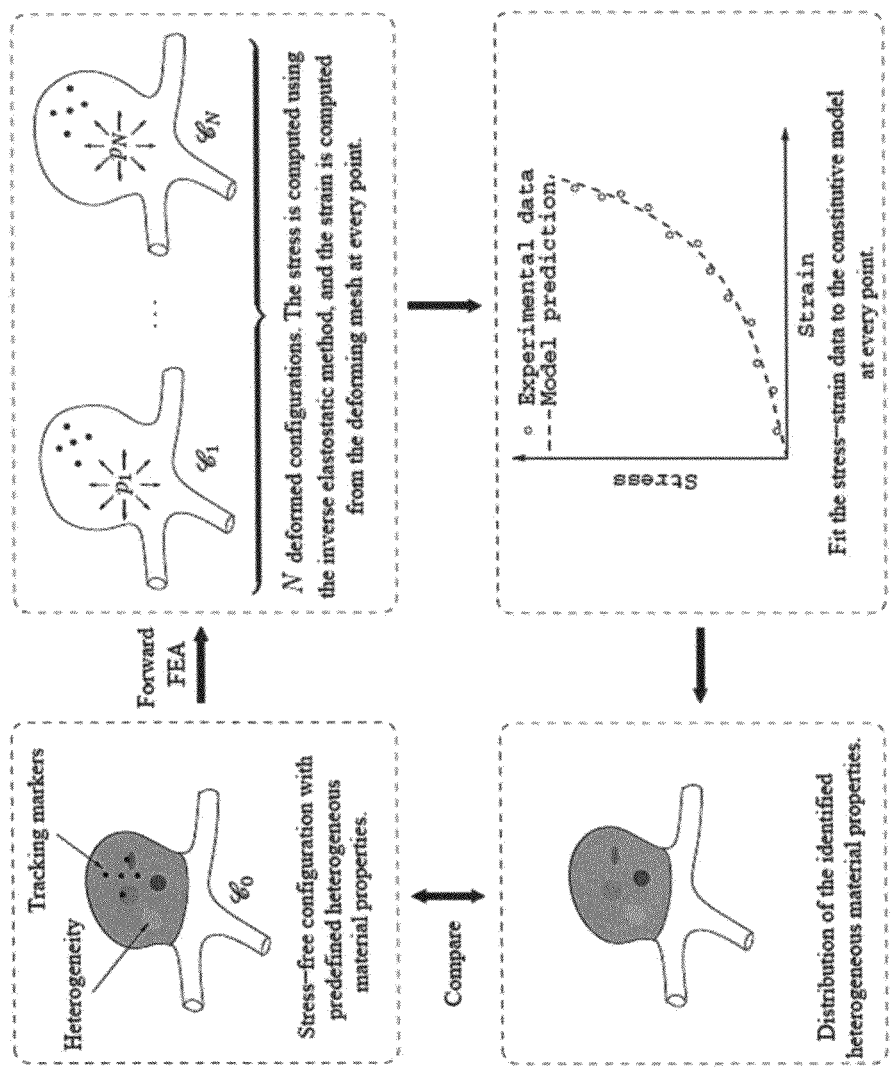
FIG. 21 illustrates a schematic of the procedure for validating the pointwise identification method in cerebral aneurysms according to the present invention.

A virtual (numerical) test is conducted to demonstrate and evaluate the utility of PWIM in cerebral aneurysms. The procedure is illustrated in FIG. 21. Forward finite element analysis is applied first to a cerebral aneurysm sac of known material property and geometry to generate a series of deformed states.

The inverse finite element formulation for membrane problems starts with the standard weak form:

$$\int_\Omega t^{\alpha\beta} g_\alpha \cdot \delta x_{,\beta} da - \int_{\partial\Omega_t} t \cdot \delta x ds - \int_\Omega pn \cdot \delta x da = 0, \quad (49)$$

which is the same as the forward analysis, where $\Omega$ is the current surface, $\partial\Omega_t$ is the boundary upon which the traction t is applied, and $\delta x$ is any kinematically admissible variation to the current configuration. In the inverse setting, the current configuration is prescribed; the weak form is solved for the material point position X in the stress-free reference configuration, which enters the weak form through the constitutive equation.

Figure 22:
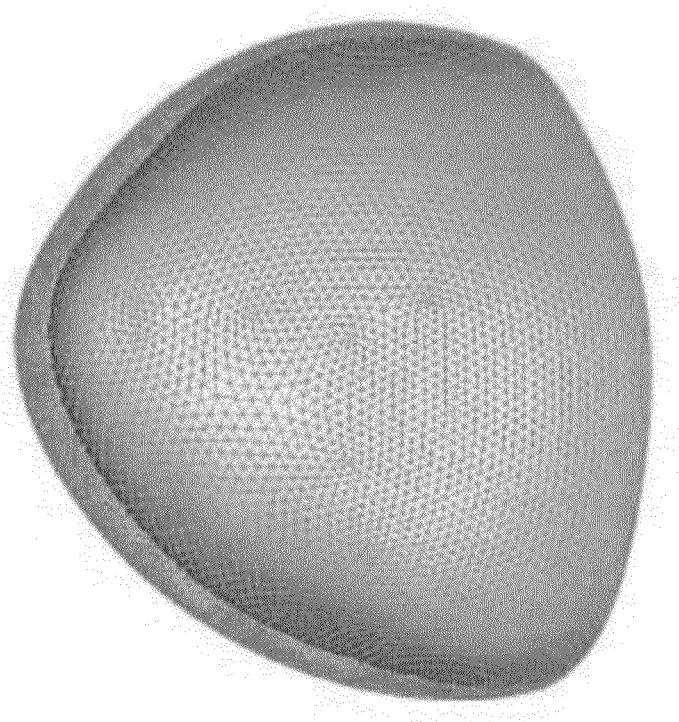
FIG. 22 illustrates the initial configuration of the cerebral aneurysm sac according to the present invention.

The FEIEM model of the aneurysm sac is shown in FIG. 22 including the initial configuration and a deformed configuration under the highest pressure (p=110 mmHg). Clamped boundary condition is applied at the neck of the aneurysm, to mimic a common setting in experiment. The assumed distribution of heterogeneous elastic property (FIG. 23) of the aneurysm wall will be referred to herein as the "realistic distribution" of the elastic properties. Taking the realistic distribution as input, an inflation motion is simulated by performing a series of quasistatic finite element analyses for the aneurysm sac. The obtained deformed configurations and assumed reference configuration are considered as "virtual" experimentally observed configurations. Subsequently, the elastic properties, which may include fiber orientation information, of the aneurysm are set to be unknown and the virtual experimental data is used to identify the elastic parameters of the selected model. After applying the pointwise identification method for each Gauss point, a distribution of identified elastic properties is obtained for the cerebral aneurysm sac. This distribution will be referred to as the "identified distribution" of the elastic properties. The next step is to compare the identified distribution to the realistic distribution to conclude whether or not the method is valid and effective.

A typical cerebral aneurysm wall consists of primarily 7-8 layers of type I and III collagen fibers with varying orientations that form two-dimensional networks. At the continuum level, the tissue is typically described by a single strain energy function that takes into account collectively the properties of the constituents and microstructure. It is assumed that the cerebral aneurysm wall is composed of random elastin network, reinforced by two families of orthogonal collagen fibers. The first family of fibers are further assumed to be parallel to the basal (x-y) plane and tangent to the aneurysm surface at every point. The second family is pointwise perpendicular to the first one. The material property of the cerebral aneurysm is assumed to be heterogeneous; the elastic stiffness decreases linearly with respect to the height from the neck (see FIG. 23).

An anisotropic structural strain energy function is used to model the elastic behavior of the cerebral aneurysm sac. The surface strain energy function (per unit reference area) takes the form $$w = k_1(I_1 - 2\log J - 2) + \sum_{i=4,6} \frac{k_i}{a}\{\exp[a(I_i - 1)^2] - 1\}, \quad (50)$$

where $k_i$ (i=1, 4, 6) are effective elastic stiffness parameters, which are the product of 3-D elasticity constants and the wall thickness, having the dimension of force per unit length. The assumed heterogeneity in the effective stiffness parameters may arise from the spatial variation of the 3-D elastic constants, the wall thickness, or a combination of both. The values of $k_4$ and $k_6$ signify the stiffness differentiation in the fiber (or preferred) directions, i.e., the horizontal direction $N_1$ and the meridional direction $N_2$. It appears that there is no established evidence on which direction exhibits stiffer behavior. It is assumed that the collagen fibers along $N_1$ are two times stiffer than those along $N_2$.

In Equation (50), $I_1$, $I_4$, $I_6$, and J are the strain invariants. It is convenience to introduced these invariants in tensorially covariant forms based on convected coordinates. In this representation, the surface is parameterized by surface coordinates $\xi^\alpha$ ($\alpha=1,2$) in which a pair of coordinates $P=(\xi^1, \xi^2)$ is regarded as the same material point during the deformation. The position vectors of the material point P in the reference configuration $C_0 \epsilon R^3$ and a deformed configuration $C \epsilon R^3$ is denoted by X=X(P) and x=x(P). The tangent vectors of the coordinate curves $$G_\alpha = \frac{\partial X}{\partial \xi^\alpha}, g_\alpha = \frac{\partial x}{\partial \xi^\alpha}$$

form the basis of the surface tangent space at X(P) and x(P), respectively. The contravariant surface basis vectors $\{G^\alpha, g^\alpha, \alpha=1,2\}$ are defined by in the standard manner. The covariant reference and current metric tensors are $G_{\alpha\beta}=G_\alpha \cdot G_\beta$ and $g_{\alpha\beta}=g_\alpha \cdot g_\beta$, respectively. The contravariant components $g^{\alpha\beta}$ the metric tensors are such that $g^{\alpha\beta}g_{\beta\gamma}=\delta_\gamma^\alpha$, and similarly for $G^{\alpha\beta}$. The surface deformation gradient, which maps the surface tangent vectors at X(P) in $C_0$ to the tangent vectors at x(P) in C, is $F=g_\alpha \otimes G^\alpha$. The right Cauchy-Green deformation tensor follows $C=F^TF=g_{\alpha\beta}G^\alpha \otimes G^\beta$.

In this curvilinear setting the aforementioned strain invariants are defined as $$I_1 = g_{\alpha\beta}G^{\alpha\beta}, J = \sqrt{\frac{g}{G}}, \quad (51)$$

where g and G are respectively the determinants of the matrices $[g_{\alpha\beta}]$ and $[G_{\alpha\beta}]$; and $$I_4 = \frac{N_1^\alpha g_{\alpha\beta}N_1^\beta}{N_1^\delta G_{\delta\gamma}N_1^\gamma}, I^6 = \frac{N_2^\alpha g_{\alpha\beta}N_2^\beta}{N_2^\delta G_{\delta\gamma}N_2^\gamma}, \quad (52)$$

where $N_1=N_1^\alpha G_\alpha$ and $N_2=N_2^\alpha G_\alpha$ are the fiber directions in the reference configuration. In this covariant setting, the fiber vectors in a current configuration are given by $n_1=N_1^\alpha g_\alpha$ and $n_2=N_2^\alpha g_\alpha$, namely, the components remain the same. Thus, the fiber directions are known if their components in a configuration are specified. Moreover, $I_4$ and $I_6$ represent the squared stretches of material line elements along the fiber directions $N_1$ and $N_2$, respectively. Due to the assumption that the two fiber directions in the reference configuration are orthogonal, $I_4$ and $I_6$ satisfy the relation $I_1=I_4+I_6$.

The wall tension t is the resultant of the Cauchy stress σ, $$t = \int_{-\frac{h}{2}}^{\frac{h}{2}} \sigma \, dh = t^{\alpha\beta}g_\alpha \otimes g_\beta, t^{\alpha\beta} = t^{\beta\alpha},$$

here h is the current thickness of the membrane. For a hyperelastic membrane, the tension follows the Doyle-Ericksen formula $$Jt^{\alpha\beta} = 2\frac{\partial w}{\partial g_{\alpha\beta}}.$$

Specializing to the energy function of Equation (50), the following tension components are obtained:

$$t^{\alpha\beta} = \frac{2}{J}k_1(G^{\alpha\beta} - g^{\alpha\beta}) + \quad (53)$$
$$\frac{4}{J}k_4\exp[a(I_4 - 1)^2](I_4 - 1)(N_1^\delta G_{\delta\gamma}N_1^\gamma)^{-1}N_1^\alpha N_1^\beta +$$
$$\frac{4}{J}k_6\exp[a(I_6 - 1)^2](I_6 - 1)(N_2^\delta G_{\delta\gamma}N_2^\gamma)^{-1}N_2^\alpha N_2^\beta,$$

where α, β, δ, γ=1,2, and repeating index implies summation. Note that the tension is a stress resultant having the dimension of force per unit length. Hereafter, it is called the "wall stress" or simply "stress".

The linearly varying stiffness of the aneurysm wall material is represented by the varying effective elasticity parameter, $k_i$ ($i=1, 4, 6$) according to $$k_i = k_i^{fundus} + \frac{k_i^{neck} - k_i^{fundus}}{Z_i^{neck} - Z_i^{fundus}}(Z - Z_i^{fundus}), \tag{54}$$

where Z is the "Z" coordinate of any point on the sac, $Z^{fudus}$ and $Z^{neck}$ are the "Z" coordinates at the fundus and neck, respectively. Similarly, $k_i$ are the elastic parameters at point "Z", $k_i^{fundus}$ and $k_i^{neck}$ are respectively the elasticity parameters at the fundus and neck, and they take the value of $k_1^{fundus}$=0.01875 N/mm, $k_1^{neck}$=0.05626 N/mm, $k_4^{fundus}$=0.03513 N/mm, $k_4^{neck}$=0.10538 N/mm, $k_6^{fundus}$=0.01171 N/mm, $k_6^{neck}$=0.03513 N/mm. (55)

The parameter a is a dimensionless number; a uniform value a=0.7112 is assumed over the entire sac.

Figure 23:
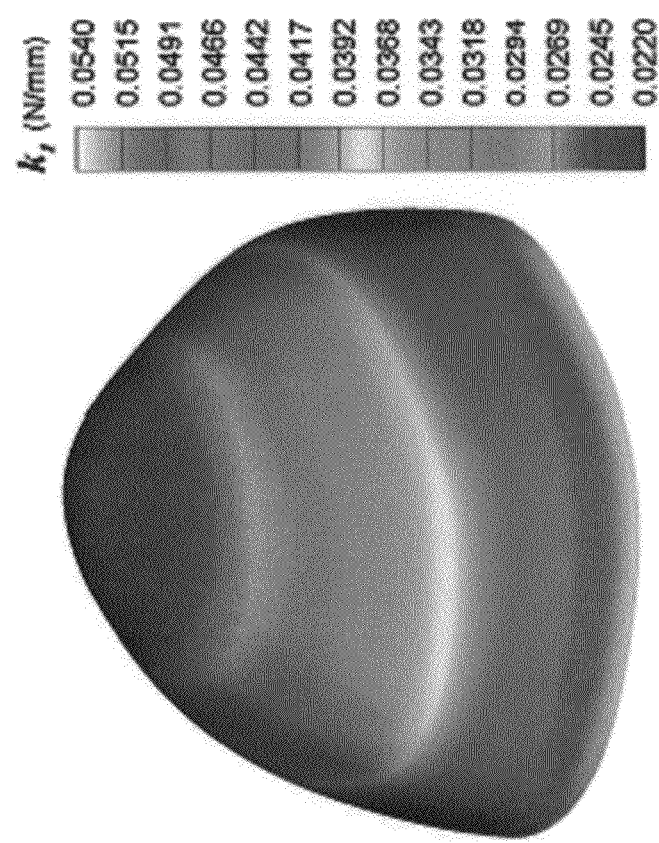
FIG. 23 illustrates the realistic (assumed) distribution of heterogeneous elastic property of the aneurysm wall according to the present invention.

Due to the scarcity of published values of the elastic parameters specific to cerebral aneurysms, the identified parameters from experiments for arteries are referred to while choosing the values of these parameters. The value of a is the same as the reported value for arterial adventitia. The reported values of $k_1$ and $k_4$ are scaled proportionally, and the value of $k_6$ is presumed based on the assumption that the stiffness along $N_1$ is two times higher than that along $N_2$, i.e. $k_4$=3$k_6$. It is worth pointing out that these parameters are chosen to generate a reasonable deformation while taking advantage of the most reliable experimental results. In the deformation range considered in cerebral aneurysms, the stress-strain relation is insensitive to the parameter a described more fully below. Thus, it is difficult to identify a using the stress-strain data. As a first step, the parameter a is known, and the elastic parameters $k_1$, $k_4$, $k_6$ are identified and possibly the fiber orientations. FIG. 23 shows the realistic (assumed) distribution of $k_1$. The realistic distribution of $k_4$ and $k_6$ has the same pattern and is not shown here.

Eleven deformed configurations were generated by applying pressures ranging from 60 to 110 mmHg at an interval of 5 mmHg. To simulate the clamped boundary constraint typically used in experiments, it is assumed that the neck of the sac is fixed. The simulation of the inflation motion was conducted using the forward nonlinear membrane finite element in a Finite Element Analysis Program (FEAP). The largest principal surface stretch, $\lambda_1$=1.12, occurs on the configuration under the highest pressure (p=110 mmHg).

Because it is assumed that the first family of collagen fibers lies parallel to the basal plane, the fibers near the fundus form closed loops with extremely small radius of curvature which presents a reinforcing effect. It turns out that the deformed surface near the fundus is almost flat, which gives difficulties in determining the stress in there by inverse analysis. Therefore, the stress determination would be inaccurate not only at the region near the clamped boundary, but the region near the fundus. It is worth noting that such phenomena arises from the assumption on the fiber direction distribution.

Following the inflation simulation of the cerebral aneurysm sac, each of the obtained deformed configurations are taken as input, and the inverse method is applied to compute the wall stress distribution. Cauchy stress was obtained at each Gauss point of the finite element mesh. An isotropic neo-Hookean constitutive model along with assumed model parameters was used to compute the wall stress. The neo-Hookean strain energy function takes the form $$w = \frac{v_1}{2}(I_1 - 2\log J - 2) + \frac{v_2}{4}(I_1 - 2)^2. \tag{56}$$

The parameters $v_1$ and $v_2$ are effective elastic parameters which are multiplications of 3-D elasticity constants with the wall thickness. $v_1 = v_2 = 5.0$ N/mm were used in the inverse FE analysis. The computed stress distributions were compared to the actual stress distribution computed from the forward FE analyses to evaluate the insensitivity of the stress with respect to the selected constitutive models and their elastic parameters.

From the nodal coordinates in the reference and deformed configurations, strain distributions in each deformed configuration can be computed with the aid of the finite element interpolation. Here, the surface inside an element is parameterized by the finite element natural coordinates, which will be used as convected surface coordinates. From the finite element interpolation, the base vectors in the deformed configuration and reference configuration are computed at each Gauss point by $$G_\alpha = \sum_{I=1}^{Nel} \frac{\partial N_I}{\partial \xi^\alpha} X^I, \quad g_\alpha = \sum_{I=1}^{Nel} \frac{\partial N_I}{\partial \xi^\alpha} x^I, \tag{57}$$

where Nel is the total number of nodes per element.

The metric tensor components in the reference configuration and deformed configuration are computed by $$G_{\alpha\beta} = \sum_{I=1}^{Nel} \sum_{I=J}^{Nel} \frac{\partial N_I}{\partial \xi^\alpha} \frac{\partial N_J}{\partial \xi^\beta} X^I \cdot X^J. \tag{58}$$

$$g_{\alpha\beta} = \sum_{I=1}^{Nel} \sum_{I=J}^{Nel} \frac{\partial N_I}{\partial \xi^\alpha} \frac{\partial N_J}{\partial \xi^\beta} x^I \cdot x^J.$$

The strain invariants in Equation (51) and Equation (52) will be computed accordingly.

As shown in Equation (53), the stress components are functions of the reference and current metric tensors, the fiber directions, and the elastic parameters appearing in the constitutive law. As described above, at each Gauss point the stress components $t^{\alpha\beta}$ and the convected components $g_{\alpha\beta}$ of the current metric tensor in each of deformed configurations can be obtained. If the stress-free configuration is known, the reference metric tensor components $G_{\alpha\beta}$ are also known. Accordingly, the strain invariants $I_1$, $I_2$, $I_4$, and $I_6$ can be computed by Equation (51) and Equation (52).

The modeled stress in the i-th configuration is denoted by $$^{(i)}t^{\alpha\beta} = t^{\alpha\beta}(\alpha, k_1, k_4, k_6, {}^{(i)}g_{\delta\gamma}, G_{\delta\gamma}, N_1^\delta, N_2^\delta). \tag{59}$$

Letting $^{(i)}\hat{t}^{\alpha\beta}$ be the "experimental" stress components obtained from the inverse analysis, the objective function is defined pointwise, as $$\Phi = \sum_{i=1}^{N} \left(^{(i)}t^{\alpha\beta} - {}^{(i)}\hat{t}^{\alpha\beta}\right){}^{(i)}g_{\alpha\gamma}{}^{(i)}g_{\beta\delta}\left(^{(i)}t^{\gamma\delta} - {}^{(i)}\hat{t}^{\gamma\delta}\right), \tag{60}$$

where, N is the total number of deformed states. In tensor notation, $\Phi = \Sigma_{i=1}^N P^{(i)}t - {}^{(i)}tP^2$. If the global stress-free configuration is known, $\Phi$ is a function of the elastic parameters only.

Alternatively, as long as the modeled and experimental stress are described in the same convected coordinate system, the cost function may be constructed as $$\Psi = \sum_{i=1}^{N} w_1\left({}^{(i)}t^{11} - {}^{(i)}\hat{t}^{11}\right) + w_2\left({}^{(i)}t^{22} - {}^{(i)}\hat{t}^{22}\right) + w_3\left({}^{(i)}t^{12} - {}^{(i)}\hat{t}^{12}\right), \quad (61)$$

where $w_i$ (i=1, . . . , 3) are weight parameters. Different weight parameters may be chosen by observing different ratios among the stress components. In the current study, the two cost functions were both used, but not at the same time discussed more fully below As mentioned briefly above, the stress is insensitive to the elastic parameter a at a=0.7112. To see this, expanding the exponential terms in the Holzapfel's strain energy function into a Taylor series to gives $$w = k_1(I_1 - 2\log J - 2) + \sum_{i=4,6} k_i\left[(I_i - 1)^2 + \frac{a}{2}(I_i - 1)^4 + \dots\right]. \quad (62)$$

At a point where the maximum deformation occurs ($\lambda_1$=1.12), the quadratic term $(I_i-1)^2 = 5.93 \times 10^{-2}$, whereas the quartic term $$\frac{a}{2}(I_i - 1)^4 = 7.03 \times 10^{-4}$$

which is about two orders of magnitude smaller than the leading term. Therefore, the strain energy and stress are very insensitive to the perturbation of a, which makes it difficult to identify a, especially when experimental error exists. Based on this fact, "a" is taken as a known parameter and excluded from regression.

Focusing on an in vitro setting in which a slightly inflated configuration is taken as a reference configuration and thus $G_{\alpha\beta}$ are known and if the fiber directions are also known, the regression problem can be described as $$\text{minimize} \quad \Phi(k_1, k_4, k_6) \text{ or } \Psi(k_1, k_4, k_6) \quad (63)$$
$$\text{subject to} \quad l \le [k_1, k_4, k_6]^T \le u.$$

Here, l and u are the lower and upper bounds of the vector of regression variables $[k_1, k_4, k_6]^T$.

If the fiber directions are not known, one more regression variable enters the identification process. In the current set-up, $N_1^1 = N_1 \cdot G^1$ and $N_1^2 = N_1 \cdot G^2$ are the components of the first fiber direction $N_1$ with respect to base vectors $G_1$ and $G_2$, respectively. Since two fiber directions are orthogonal in the stress-free configuration, the components ($N_2^1$ and $N_2^2$) for the second fiber direction $N_2$ are determined explicitly. Therefore, the identification of the fiber directions can be realized by identifying only one fiber direction, say $N_1$.

From Equation $(52)_\alpha$, it is known that $I_4$ depends only on the ratio between $N_1^1$ and $N_1^2$, and thus so for $I_6$. In the parameter regression process, first $N_1^1$ is set to be 1, and $N_1^2$ is identified. If the realistic value of $N_1^1$ is comparable to 1, $N_1^2$ can be identified successfully. However, if the realistic value of $N_1^1$ is close to 0 and that of $N_1^2$ is close to $\pm 1$, the ratio $|N_1^2/N_1^1| \gg 1$. If this happens, $N_1^2$ is set to be 1 and identify $N_1^1$. The parameter identification is performed by a gradient-based, sequential quadratic programming (SQP) algorithm, such as SNOPT.

Figure 24:
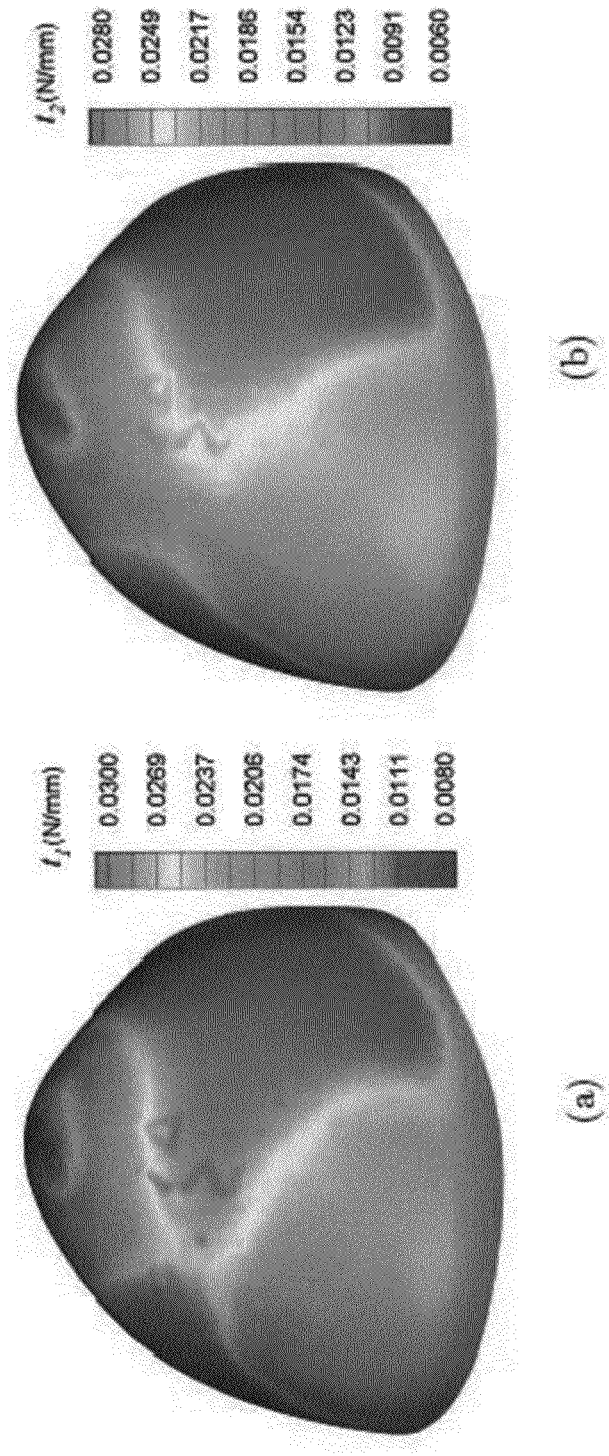
FIG. 24 illustrates the distribution of the principal stresses on the deformed configuration according to the present invention.
Figure 25:
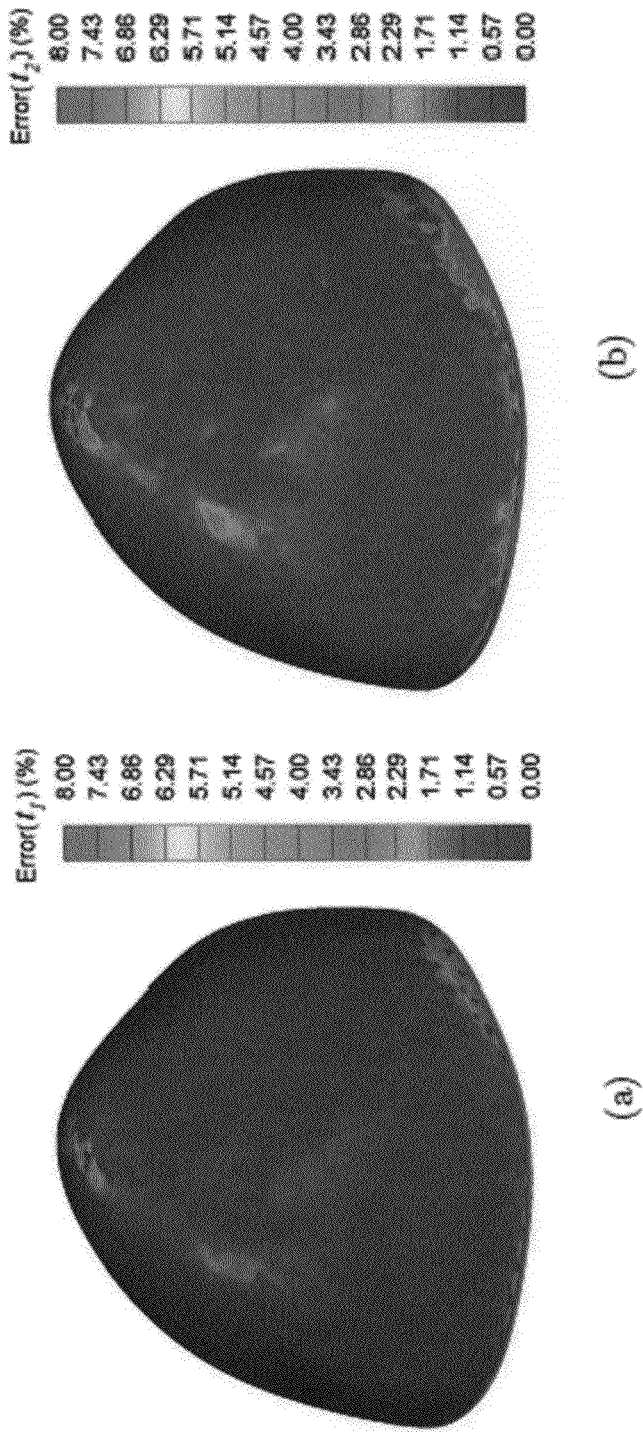
FIG. 25 illustrates the absolute percentage difference between the computed principal stresses according to the present invention.
Figure 26:
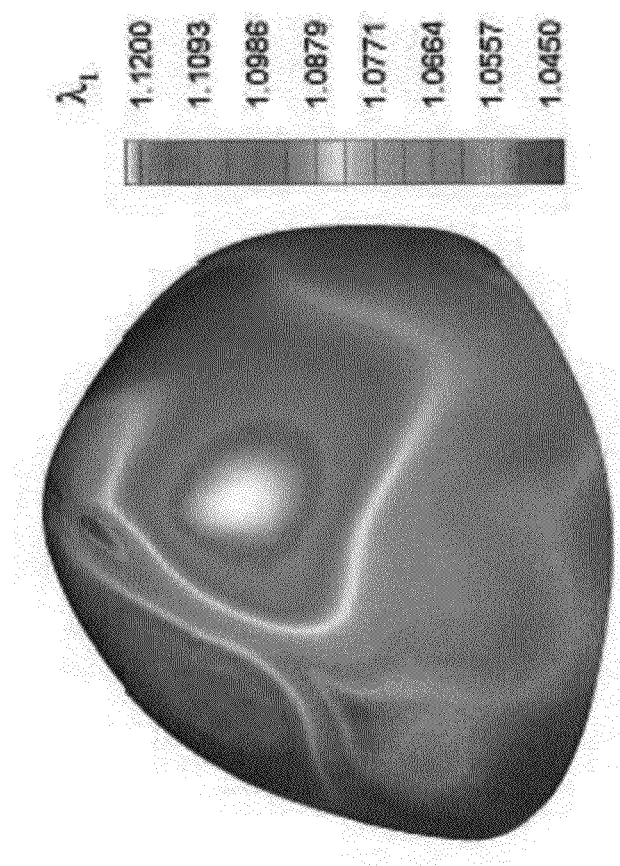
FIG. 26 illustrates the distribution of the first principal stretch according to the present invention.

Before identifying the elastic parameters, it must be verified that the wall stress obtained from inverse analysis is truly insensitive to the material property. The principal stresses in a deformed configuration (p=110 mmHg) computed from forward FEA with the anisotropic Holzapfel model are denoted as $t_i^{for}$, (i=1,2). The principal stresses in the same deformed configuration computed from inverse FEA with the isotropic neo-Hookean model are denoted as $t_i^{inv}$, which are shown in FIG. 24. A quantity $$e_i = \left|\frac{t_i^{inv} - t_i^{for}}{t_i^{for}}\right| \times 100\%, \ (i = 1, 2)$$

is used to evaluate the percentage difference between $t_i^{inv}$ and $t_i^{for}$. FIG. 25 shows the distribution of $e_i$ with FIG. 25(*a*) illustrating the error of $t_1$ and FIG. 25(*b*) illustrating the error of $t_2$. As can be seen from FIG. 25, in the most part of the sac (excluding the near-boundary region, the fundus region, and a narrow stripe along the meridional direction (displayed in light blue)), $e_1$ and $e_2$ are less than 1%. Within the stripe, they are in the order of 2%. In this region the strain is also relatively small ($\lambda_1 \approx 1.07$), and this region turns out to be where the parameter identification is relatively inaccurate as described more fully below. The distribution of the first principal stretch is shown in FIG. 26. The distribution of $e_i$ induced by increasing $v_1$ and $v_2$ shows no significant change. The fact that stress is insensitive to the material property has been revealed again. This fact is especially valuable in that it allows one to arbitrarily choose a constitutive model and use it to compute membrane stress before suitable constitutive models can be determined. Therefore, the obtained wall stress data can be used to represent the realistic stress data for the purpose of elastic parameter identification.

Parameter identification was conducted for all the Gauss points in the whole sac using the cost function $\Phi$ of Equation (60). The identified parameters are compared to the exact parameters and the elements extracted where the identification error of $k_4$ exceeded 3%. Subsequently, the parameter identification is repeated using the cost function $\Psi$ of Equation (61) for the Gauss points in the selected elements. The weights $w_i$ were chosen according to the ratios among the experimental stress components, i.e. $|\hat{t}^{11}/\hat{t}^{22}|$ and $|\hat{t}^{11}/\hat{t}^{12}|$, so as to fairly consider the influence of all the stress component on the objective function value by scaling them to a similar order. The results showed improvement in most points. After identification, the parameters at Gauss points are projected to the nodes using a least-square algorithm for a more convenient demonstration.

Figure 27:
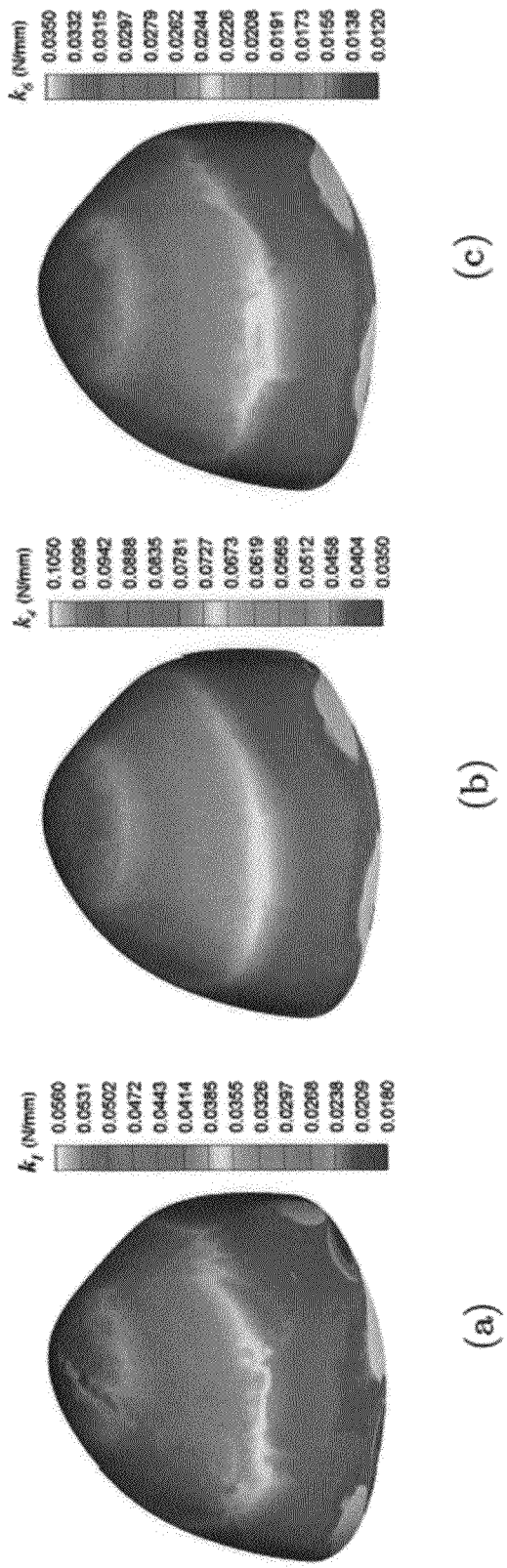
FIG. 27 illustrates the distribution of the identified elastic parameters according to the present invention.
Figure 28:
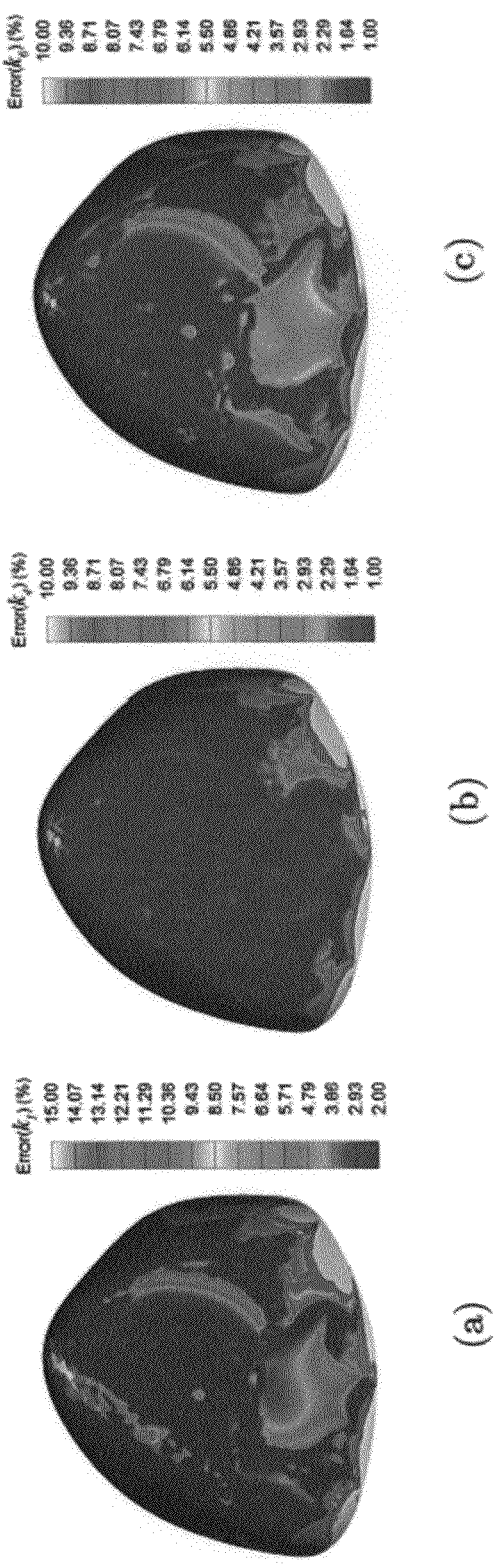
FIG. 28 illustrates the distribution of the identification errors of the elastic parameters according to the present invention.

FIG. 27 shows the distribution of the identified parameters $k_i$—specifically FIG. 27(*a*) shows the distribution of $k_1$, FIG. 27(*b*) shows the distribution of $k_4$ and FIG. 27(*c*) shows the distribution of $k_6$. As shown, the linear dependence of the identified $k_i$ on the height was recovered. The identification errors between the identified parameters and the realistic ones were computed at each nodal point according to $$\text{Error}(k_i) = \left|\frac{k_i - \tilde{k}_i}{\tilde{k}_i}\right| \times 100\%, \ (i = 1, 4, 6),$$

where $k_i$ and $\tilde{k}_i$ are identified and realistic elastic parameters, respectively. FIG. 28 shows the distributions of the identification errors of $k_1$, $k_4$ and $k_6$ respectively. The errors are less than 8%, 3% and 5% for $k_1$, $k_4$ and $k_6$, respectively, in the bulk region of the aneurysm sac. Consistently with the regions where the stress computation is not accurate, the identification is less accurate at the boundary area and the fundus. In addition, the identification is less accurate in the region where the stretch is relatively low ($\lambda_1 < 1.08$), i.e., the neck region and the meridional stripe illustrated in the contour plot of the first principal stretch (see FIG. 26). Generally, relatively bigger error occurs where the deformation is relatively smaller. The means, minimums and maximums of the identification errors over the whole sac are listed in Table 6. The maximum error occurs near the boundary, and large error only occurs at scattered spots. The mean errors for the three parameters are 6.41%, 3.50% and 4.08%, respectively.

TABLE 6

Means, minimums and maximums of the identification errors of the pointwise identification by assuming the fiber orientation is known.

|  | Error($k_1$) | Error($k_4$) | Error($k_6$) |
| --- | --- | --- | --- |
| Mean (%) | 6.41 | 3.50 | 4.08 |
| Min (%) | $1.45 \times 10^{-4}$ | $8.66 \times 10^{-5}$ | $7.17 \times 10^{-4}$ |
| Max (%) | 124.1 | 78.81 | 78.81 |

Figure 29:
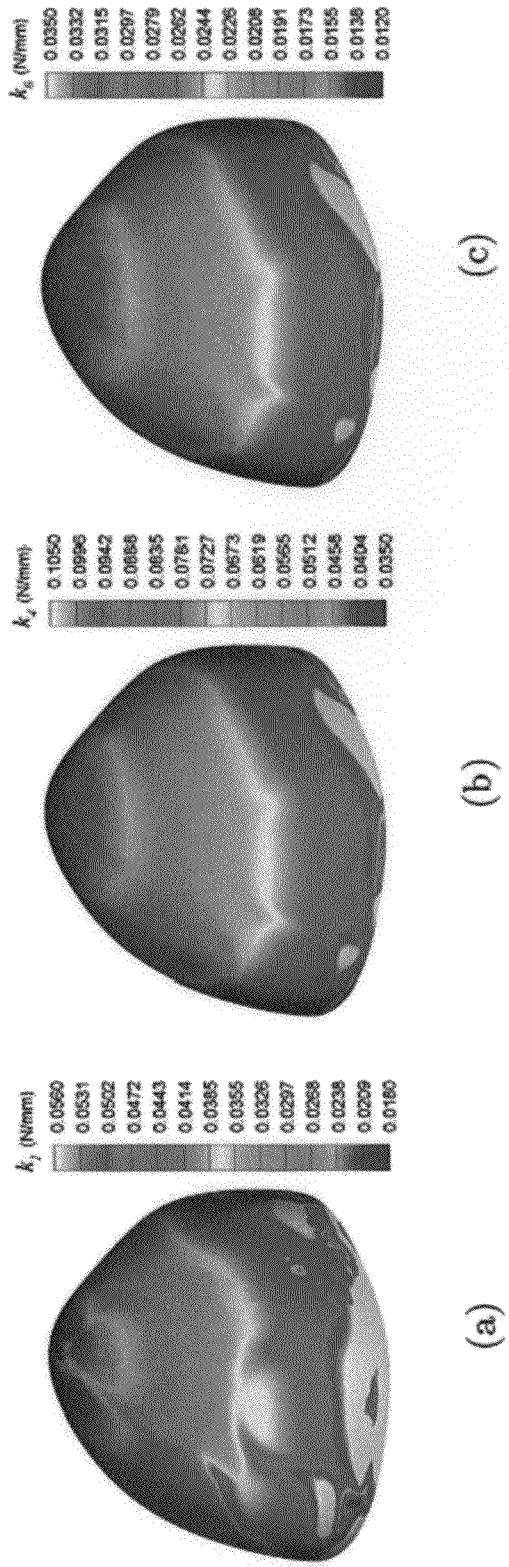
FIG. 29 illustrates the distribution of identified elastic parameters according to the present invention.

When assuming the fiber orientation to be unknown, the elastic parameters $k_i$ were identified along with $N_1^{\ 1}$ (or $N_1^{\ 2}$) by using the objective function $\Phi$. FIG. 29 shows the distribution of the identified parameters $k_i$. From a qualitative point of view, the regional variation of the elastic parameters was successfully identified. Quantitatively, the absolute identification errors for $k_1$, $k_4$ and $k_6$ were respectively less than 5%, 2% and 2% in the bulk region of the aneurysm sac. The means, minimums and maximums of the identification errors over the whole sac are listed in Table 7. The mean errors for the three parameters are 10.35%, 4.15% and 4.15%, respectively. Compare to the case of known fiber directions, the mean errors for all the parameters are larger although the elevation is not significant. This is understandable since there is one more parameter in the regression. The distributions of the identification errors follow the same pattern in FIG. 28 and are not plotted.

TABLE 7

Means, minimums and maximums of the identification errors of the pointwise identification by assuming the fiber orientation is unknown.

|  | Error($k_1$) | Error($k_4$) | Error($k_6$) |
| --- | --- | --- | --- |
| Mean (%) | 10.35 | 4.15 | 4.15 |
| Min (%) | $2.08 \times 10^{-3}$ | $5.20 \times 10^{-5}$ | $7.79 \times 10^{-5}$ |
| Max (%) | 122.9 | 63.0 | 63.04 |

Figure 30:
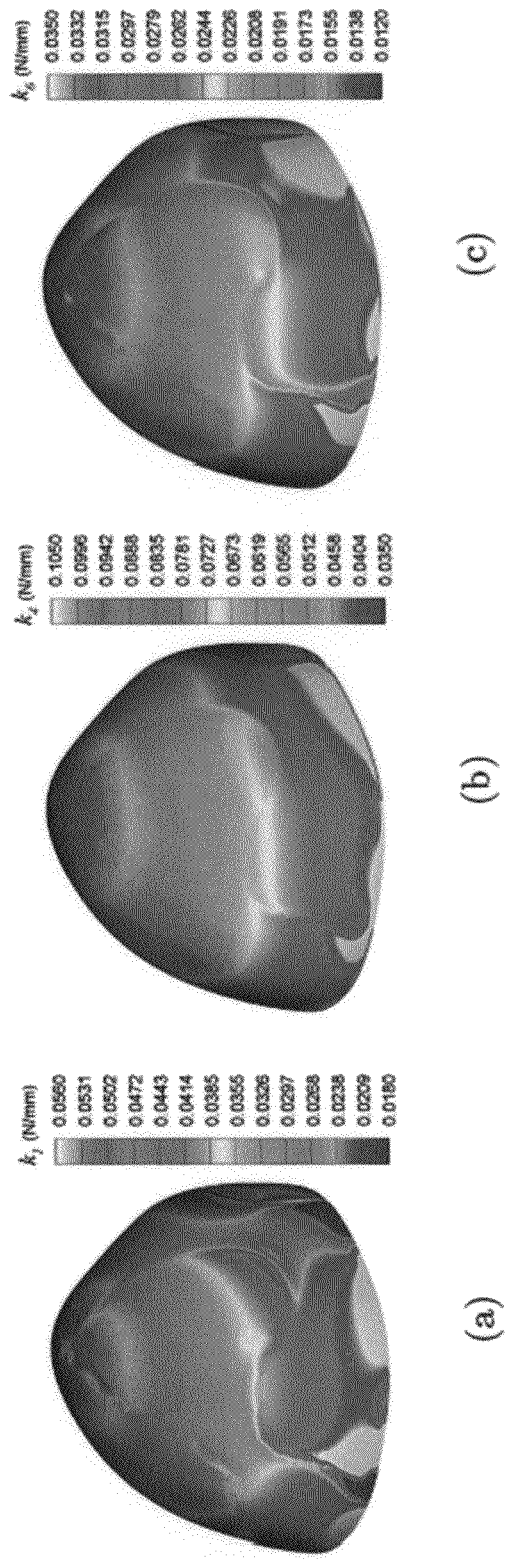
FIG. 30 illustrates the distribution of identified elastic parameters according to the present invention.

The proposed pointwise method can be modified to render a region-wise identification. Region-wise means assuming the material property is homogeneous within a region of specific size, and letting the cost function include the stress-strain data at all the Gauss points in that region. The logic is keen to that of the subdomain inverse finite element method although the implementation is entirely different. FIG. 30 shows the distribution of the identified elastic parameters by region-wise identification. The small region was chosen to be each element. The identification was conducted by using the cost function $\Phi$ alone, but including all the Gauss points within each element. The identification accuracy is almost identical to that of the pointwise scheme when using the single objective function $\Phi$ because the element size is very small. The identification error is quite small in most part of the sac. The identification error of $k_1$, $k_4$ and $k_6$ is below 4.0%, 2.5% and 4.0%, respectively, in most part of the sac. As the results show, the element-wise identification still can characterize the material heterogeneity relatively accurately as long as the specified homogeneous regions are small enough. The maximums, minimums, and means of the identification errors over the whole sac are listed in Table 8. The mean errors for the three parameters are 10.83%, 4.52% and 8.31%, respectively.

TABLE 8

Means, minimums and maximums of the identification errors of the region-wise identification by assuming the fiber orientation is known.

|  | Error($k_1$) | Error($k_4$) | Error($k_6$) |
| --- | --- | --- | --- |
| Mean (%) | 10.83 | 4.52 | 8.31 |
| Min (%) | $2.39 \times 10^{-4}$ | $1.51 \times 10^{-5}$ | $1.11 \times 10^{-3}$ |
| Max (%) | 100.0 | 81.05 | 90.49 |

The present invention effectively separates stress solution from parameter regression. The stress distributions are determined prior to parameter identification. Therefore, there is the opportunity to examine the stress-strain curves and select an appropriate mathematical function accordingly, instead of assuming an energy form a priori. This is important in practice, especially when no prior reports of tissue behavior exist. Material parameters are characterized pointwise directly from stress-strain data, consistent with the common experimental practice. In this manner, heterogeneous properties are delineated point-by-point in parallel, without coupling to each other. The decoupling of stress computation and parameter regression is the key advantage of the proposed method according to the present invention. It allows the characterization of the heterogenous properties in a simple, effective manner. In addition, the method applies to a thin tissue organ in its natural intact state, without cutting or flattening.

The numerical experiments demonstrated the feasibility of identifying the fiber directions from stress-strain data. In theory, characterizing material anisotropy involves two tasks: (1) identifying the symmetry group (e.g., isotropy, transversely isotropy, orthotropy, etc.), and (2) identifying the structural information (e.g., the fiber directions) associated with the material anisotropy. The former dictates the permissible function forms that contain the desired material symmetry while the simulation suggested that the fiber directions may be identified under the assumption of known symmetry group (which is encoded in the assumed constitutive form). For certain classes of materials, the elastic stress and deformation should obey certain universal relations involving no material property information. By examining if corresponding universal relations hold true, the type of material symmetry may be determined. Universal relations may be used for symmetry characterization for these orthotropic materials.

It should be noted that it was assumed that the reference configuration of the sac is known. While this assumption is reasonable in simulating an in vitro experimental setting, it cannot be adopted in in vivo applications because a cerebral aneurysm is eternally pressurized in its service life and, the stress-free configuration cannot be obtained from in vivo measurements. To characterize the elastic properties using in vivo data, assuming available, the stress-free configuration must be identified at least locally. It has been shown that the stress-free configuration can be represented locally by a metric tensor and thus, in theory, can be included as unknown model parameters to be estimated. The elastic parameter identification was more accurate in the high-strain region ($\lambda_1 \geq 1.08$) than in the low-strain region ($\lambda_1 < 1.08$). In fact, the strain range (10%) has already exceeded the physiological strain typical of cerebral aneurysms (2-5%). The influence of strain range is not unexpected. The reason is that the realistic parameters in the constitutive model are supposed to model the elastic behavior of the material in any deformation range. However, due to the inevitable experimental error in determining the membrane surface geometry and the position of tracking markers and the induced error in determining the realistic stress and strain distribution, certain values of the elastic parameters may render a local minimum of the objective function at a small-strain point, which may not predict the elastic response in high-strain range at that point. This highlights the limitation that the elastic behavior is not fully represented at the points where the deformation is relatively small. Nevertheless, it is worth-noting that, even if the physiological strain is low, the elastic properties identified as such may still fulfill a good predictor for the realistic motions since they are characterized from the physiological deformation. Moreover, although the strain range is higher than the physiological range, the conclusion about the feasibility of the method should remain valid since the strain values are more or less proportionally elevated.

According to the present invention, it was assumed that the fiber in the circumferential direction is stiffer for demonstrative purposes. It should be noted that the assumptions on fiber direction and stiffness difference have no effect on the demonstrated capability. The identified stiffness parameters $k_1$, $k_4$ and $k_6$ as described above are effective parameters which are the products of the intrinsic 3-D elasticity parameters and the wall thickness. In order to obtain the intrinsic 3-D elasticity parameters, the wall thickness needs to be determined.

The features of the proposed method demonstrate the feasibility of identifying the distribution of anisotropic heterogeneous elastic properties in a cerebral aneurysm wall at the organ level. In vivo identification can be realized based on the method according to the present invention as long as the technology allows the registration of the dynamic deformation of the membrane surface in question.

Figure 31:
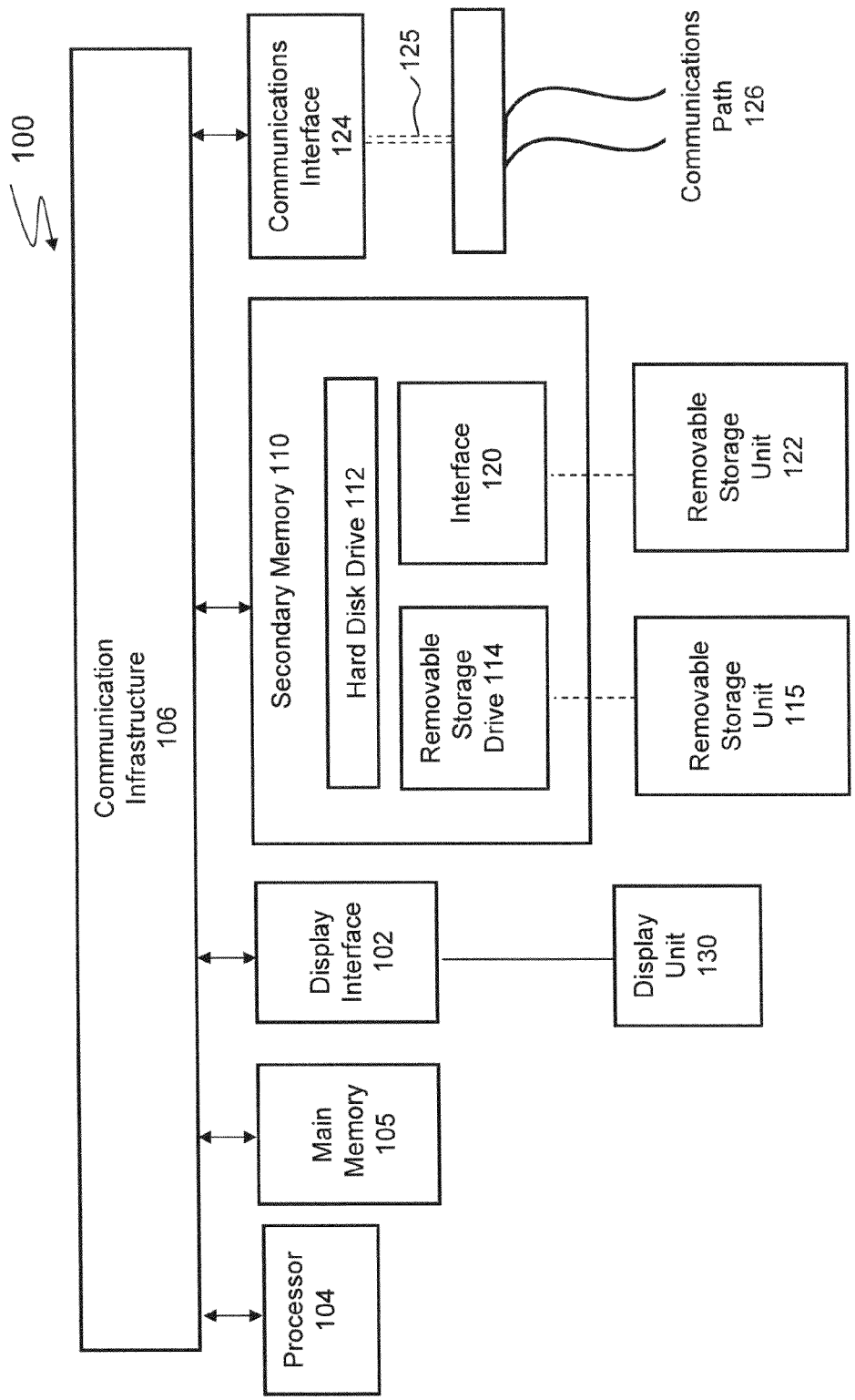
FIG. 31 illustrates an exemplary computer system, or network architecture, that may be used to implement the methods according to the present invention.

FIG. 31 illustrates an exemplary computer system 100, or network architecture, that may be used to implement the methods according to the present invention. One or more computer systems 100 may carry out the methods presented herein as computer code. One or more processors, such as processor 104, which may be a special purpose or a general-purpose digital signal processor, is connected to a communications infrastructure 106 such as a bus or network. Computer system 100 may further include a display interface 102, also connected to communications infrastructure 106, which forwards information such as graphics, text, and data, from the communication infrastructure 106 or from a frame buffer (not shown) to display unit 130. Computer system 100 also includes a main memory 105, for example random access memory (RAM), read-only memory (ROM), mass storage device, or any combination thereof. Computer system 100 may also include a secondary memory 110 such as a hard disk drive 112, a removable storage drive 114, an interface 120, or any combination thereof. Computer system 100 may also include a communications interface 124, for example, a modem, a network interface (such as an Ethernet card), a communications port, a PCMCIA slot and card, wired or wireless systems, etc.

It is contemplated that the main memory 105, secondary memory 110, communications interface 124, or a combination thereof function as a computer usable storage medium, otherwise referred to as a computer readable storage medium, to store and/or access computer software and/or instructions.

Removable storage drive 114 reads from and/or writes to a removable storage unit 115. Removable storage drive 114 and removable storage unit 115 may indicate, respectively, a floppy disk drive, magnetic tape drive, optical disk drive, and a floppy disk, magnetic tape, optical disk, to name a few.

In alternative embodiments, secondary memory 110 may include other similar means for allowing computer programs or other instructions to be loaded into the computer system 100, for example, an interface 120 and a removable storage unit 122. Removable storage units 122 and interfaces 120 allow software and instructions to be transferred from the removable storage unit 122 to the computer system 100 such as a program cartridge and cartridge interface (such as that found in video game devices), a removable memory chip (such as an EPROM, or PROM) and associated socket, etc.

Communications interface 124 allows software and instructions to be transferred between the computer system 100 and external devices. Software and instructions transferred by the communications interface 124 are typically in the form of signals 125 which may be electronic, electromagnetic, optical or other signals capable of being received by the communications interface 124. Signals 125 are provided to communications interface 124 via a communications path 126. Communications path 126 carries signals 125 and may be implemented using wire or cable, fiber optics, a phone line, a cellular phone link, a Radio Frequency (RF) link or other communications channels.

Computer programs, also known as computer control logic, are stored in main memory 105 and/or secondary memory 110. Computer programs may also be received via communications interface 124. Computer programs, when executed, enable the computer system 100, particularly the processor 104, to implement the methods according to the present invention. The methods according to the present invention may be implemented using software stored in a computer program product and loaded into the computer system 100 using removable storage drive 114, hard drive 112 or communications interface 124. The software and/or computer system 100 described herein may perform any one of, or any combination of, the steps of any of the methods presented herein. It is also contemplated that the methods according to the present invention may be performed automatically, or may be invoked by some form of manual intervention The invention is also directed to computer products, otherwise referred to as computer program products, to provide software to the computer system 100. Computer products store software on any computer useable medium. Such software, when executed, implements the methods according to the present invention. Embodiments of the invention employ any computer useable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems (MEMS), nanotechnological storage device, etc.), and communication mediums (e.g., wired and wireless communications networks, local area networks, wide area networks, intranets, etc.). It is to be appreciated that the embodiments described herein can be implemented using software, hardware, firmware, or combinations thereof.

The computer system 100, or network architecture, of FIG. 31 is provided only for purposes of illustration, such that the present invention is not limited to this specific embodiment. It is appreciated that a person skilled in the relevant art knows how to program and implement the invention using any computer system or network architecture.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A method for identifying heterogeneous wall elastic properties in a thin-walled material structure, comprising the steps of:
   computing stress distribution in each deformed configuration of a plurality of deformed configurations individually by measuring deformation of the thin-walled material structure to obtain a deformed configuration, formulating a stress-equilibrium problem on the deformed configuration, and executing a stress computation to solve for a wall stress distribution by way of finding the undeformed configuration using assumed material properties;
   calculating surface strain distribution relative to an un-inflated configuration or a slightly inflated configuration using information of surface deformation;
   obtaining stress-strain data;
   examining one or more stress-strain curves to select a mathematical function to fit the stress-strain data; and
   acquiring the best fit material parameters point-by-point by fitting the stress-strain data point-wisely.

2. The method for identifying heterogeneous wall elastic properties in a thin-walled material structure according to claim 1, wherein said computing step further comprises the step of determining the stress distribution using information of the deformed configuration and an applied pressure as input.

3. The method for identifying heterogeneous wall elastic properties in a thin-walled material structure according to claim 1, wherein said calculating step further comprises the steps of:
   selecting a reference configuration including reference geometry; and
   ascertaining the surface strain distribution from a displacement to the reference geometry.

4. The method for identifying heterogeneous wall elastic properties in a thin-walled material structure according to claim 1, wherein said examining step further comprises the steps of:
   postulating a stress-strain function of the surface strain distribution; and
   deriving a stress-strain relation from a strain-energy function.

5. The method for identifying heterogeneous wall elastic properties in a thin-walled material structure according to claim 4, wherein said acquiring step further comprises the step of formulating a nonlinear regression problem to fit the stress-strain data to the stress-strain function.

6. The method for identifying heterogeneous wall elastic properties in a thin-walled material structure according to claim 1, wherein said acquiring step further comprises the step of classifying the best fit material parameters at multiple points in parallel to delineate the distribution of the heterogeneous wall elastic properties.

7. A method for computing stress of a thin-walled material structure, comprising the steps of:
   (a) measuring deformation of the thin-walled material structure to obtain a deformed configuration;
   (b) formulating a stress-equilibrium problem on the deformed configuration; and
   (c) executing a stress computation to solve for a wall stress distribution by way of finding the undeformed configuration using assumed material properties; and
   (d) performing a sensitivity analysis to identify one or more regions where the wall stress distribution of the deformed configuration is insensitive to material parameters used in the stress computation.

* * * * *